(12) United States Patent
Atkin et al.

(10) Patent No.: US 7,846,654 B2
(45) Date of Patent: Dec. 7, 2010

(54) USES OF SPOROPOLLENIN

(75) Inventors: Stephen Lawrence Atkin, Hull (GB); Stephen Thomas Beckett, Wigginton (GB); Grahame Mackenzie, Hull (GB)

(73) Assignee: University of Hull, Hull (GB)

( * ) Notice: Subject to any disclaimer, the term of this patent is extended or adjusted under 35 U.S.C. 154(b) by 184 days.

(21) Appl. No.: 12/020,444

(22) Filed: Jan. 25, 2008

(65) Prior Publication Data

US 2008/0188572 A1 Aug. 7, 2008

Related U.S. Application Data

(63) Continuation-in-part of application No. PCT/GB2006/002800, filed on Jul. 27, 2006.

(30) Foreign Application Priority Data

Jul. 28, 2005 (GB) ................................. 0515521.3
Aug. 10, 2005 (GB) ................................. 0516397.7

(51) Int. Cl.
C12Q 1/00 (2006.01)
(52) U.S. Cl. .......................................................... 435/4
(58) Field of Classification Search ........................ None
See application file for complete search history.

(56) References Cited

U.S. PATENT DOCUMENTS

| 5,013,552 | A | 5/1991 | Amer et al. |
| 5,275,819 | A | 1/1994 | Amer et al. |
| 5,648,101 | A | 7/1997 | Tawashi |
| 6,156,330 | A | 12/2000 | Tsukada et al. |
| 6,342,255 | B1 * | 1/2002 | De Gregorio ............... 424/778 |
| 7,608,270 | B2 | 10/2009 | Beckett et al. |
| 2005/0002963 | A1 | 1/2005 | Beckett et al. |
| 2008/0311213 | A1 | 12/2008 | Atkin et al. |
| 2009/0246125 | A1 | 10/2009 | Atkin et al. |

FOREIGN PATENT DOCUMENTS

| CN | 1 105 594 | 7/1995 |
| DE | 199 02 724 A1 | 7/2000 |
| DE | 102 16 772 A1 | 10/2003 |
| GB | 0427520.2 | 12/2004 |
| WO | WO99/49063 | 9/1999 |
| WO | WO 02/055561 A1 | 7/2002 |
| WO | WO 03/078048 A2 | 9/2003 |
| WO | WO 03/094942 A1 | 11/2003 |
| WO | WO 2005/000280 A2 | 1/2005 |
| WO | WO 2005/000280 A3 | 1/2005 |
| WO | WO 2006/064227 | 6/2006 |
| WO | WO 2007/012856 | 2/2007 |
| WO | WO 2007/012857 | 2/2007 |

OTHER PUBLICATIONS

Oden et al. "Demonstration of superoxide dismutase enzymes in extracts of pollen and anther of Zea mays and in two related products, Baxtin and Polbax", Grana, 1992, 31:76-80.*
US Office Action dated Feb. 6, 2007 issued in U.S. Appl. No. 10/877,042.
US Final Office Action dated Oct. 16, 2007 issued in U.S. Appl. No. 10/877,042.
US Office Action dated May 5, 2008 issued in U.S. Appl. No. 10/877,042.
US Office Action (Interview Summary) dated Oct. 16, 2008 issued in U.S. Appl. No. 10/877,042.
US Final Office Action dated Nov. 7, 2008 issued in U.S. Appl. No. 10/877,042.
US Office Action (Advisory Action) dated Dec. 22, 2008 issued in U.S. Appl. No. 10/877,042.
US Office Action (Interview Summary) dated Mar. 9, 2009 issued in U.S. Appl. No. 10/877,042.
US Notice of Allowance dated Jun. 22, 2009 issued in U.S. Appl. No. 10/877,042.
International Search Report dated Apr. 25, 2005 issued in PCT/GB2004/002775.
International Preliminary Report on Patentability and Written Opinion dated Jan. 3, 2006 issued in PCT/GB2004/002775.
PCT Written Opinion dated Mar. 24, 2006 issued in PCT/GB2005/004824 (WO 2006/064227).
PCT International Search Report dated Mar. 27, 2006 issued in PCT/GB2005/004824 (WO 2006/064227).
PCT International Preliminary Report on Patentability dated Jun. 19, 2007 issued in PCT/GB2005/004824 (WO 2006/064227).
PCT International Search Report dated Oct. 13, 2006 issued in PCT/GB2006/002800 (WO 2007/012856).
PCT International Preliminary Report on Patentability and Written Opinion dated Jan. 28, 2008 issued in PCT/GB2006/002800 (WO 2007/012856).

(Continued)

*Primary Examiner*—Karen Cochrane Carlson
*Assistant Examiner*—Bin Shen
(74) *Attorney, Agent, or Firm*—Weaver Austin Villeneuve & Sampson LLP

(57) ABSTRACT

This invention provides the use of an exine shell of a naturally occurring spore, or a fragment thereof, as an antioxidant, for instance in a composition or formulation containing an active substance. Also provided is a method for reducing rancidity, or other oxidative degradation, of a substance, composition, or formulation, by encapsulating the substance, composition, or formulation in, or chemically binding it to, or mixing it with, an exine shell of a naturally occurring spore or a fragment thereof.

25 Claims, No Drawings

OTHER PUBLICATIONS

International Search Report dated Oct. 13, 2006 issued in PCT/GB2006/002802 (WO 2007/012857).
International Preliminary Report on Patentability and Written Opinion dated Jan. 29, 2008 issued in PCT/GB2006/002802 (WO 2007/012857).
UK Search Report and Examination Opinion dated Dec. 7, 2005 issued in GB0516397.7.
UK Search Report dated Dec. 15, 2003 issued in GB 0315019.0.
Adamson et al., (Nov. 1983) "New applications of sporopollenin as a solid phase support for peptide synthesis and the use of sonic agitation" *International Journal of Peptide and Protein Research*, 22(5):560-564.
Ahlers et al., (Mar.-Apr. 2000) "The Nature of Oxygen in Sporopollenin from the Pollen of *Typha angustifolia* L.", *Journal of Biosciences*, 55(3-4):129-136.
Bohne et al., (2003) "Diffusion Barriers of Tripartite Sporopollenin Microcapsules Prepared from Pine Pollen", *Annals of Botany* 92:289-297.
Clark, Andy (Sep./Oct. 2002) "Formulation of proteins and peptides for inhalation", *dds&s*, 2(3):73-77.
Crockford et al., (Dec. 2002/Jan. 2003) "Adaptive Aerosol Delivery (AAD$^{TM}$) technology: drug delivery technology that adapts to the patient", *dds&s*, 2(4):110-113.
Fenyvesi et al., (Feb. 17, 2004) "Synthesis and characterization of tubular amphiphilic networks with controlled pore dimensions for insulin delivery", http://wost.wok.mimas.ac.uk:8000/C1W.cgi.
Gregoriadis, Gregory (Dec. 2002/Jan. 2003) "Liposomes in drug and vaccine delivery", *dds&s*, 2(4):91-97.
Hamilton et al., (1984) "Survey for Prunus Necrotic Ringspot and Other Viruses Contaminating the Exine of Pollen Collected by Bees", *Canadian Journal of Plant Pathology*, 6(3):196-199.
Ivleva et al., (2005) "Characterization and discrimination of Pollen by Raman microscopy", *Analytical and Bioanalytical Chemistry*, 381(1):261-267.
Jorde et al., (1974) "ZUR Persorption Von Pollen UND Sporen Durch Die Intake Darmschleimhuat", *Acta Allergologica*, 29:165-175.
Penny, J. (Dec. 2002/Jan. 2003) "Bioavailability of orally delivered therapeutics: a biological perspective", *dds&s*, 2(4):100-102.
Polysciences, Inc., (Oct. 1999) "Sporopollenin Microparticles", *Technical Data Sheet* 281:1-2.
Reslow et al., (Dec. 2002/Jan. 2003) "Sustained-release of human growth hormone from PLG-coated starch microspheres", *dds&s*, 2(4):103-109.
Shaw et al, (Nov. 1, 1988) "The Use of Modified Sporopollenin from *Lycopodium clavatum* as a Novel Ion-or Ligand-Exchange Medium", *Reactive Polymers* 9(2):211-217.
Smith, Ian (Dec. 2002/Jan. 2003) "Bioavailability, targeting and controlled release—the key to effective drug delivery?", *dds&s*, 2(4):89.
Soler et al., (1977) "Technical procedure for tagged pollen aerosols for the study of their penetration in the bronchial tree", *Clinical Respiratory Physiology*, France, 13(4):499-511.
"Sporomex Ltd: oral and respirable drug delivery", Page last modified on Mar. 2, 2005, www.sporomex.co.uk, 5 pages.
Stanley, R.G., Linskens H.F. (*1974*) Pollen: Biology, Biochemistry Management, New York, Springer-Verlag, 114-115, 179-181.
Volkheimer et al., (1967) "Le phénomène de la Persorption et son importance en Allergologie", *Maroc. Med.*, 47:626-633.
Weiner, M.L., (1998) "Intestinal Transport of Some Macromolecules in Food", *Fd Chem. Toxic*, 26(10):867-880.
Wiseman, Alan (Dec. 2002/Jan. 2003) "Targeted membrane-penetrating peptides: identify candidate drug- cargoes in silico?", *dds&s*, 2(4):114.
Wiseman, Alan (Dec. 2002/Jan. 2003) "Cell-Penetrating Peptides. Processes and Applications", *dds&s*, 2(4):115.
Wittborn et al., (1998) "Nanoscale Similarities in the Substructure of the Exines of *Fagus* Pollen Grains and *Lycopodium* Spores", *Annals of Botany* 82:141-145.

* cited by examiner

USES OF SPOROPOLLENIN

CROSS-REFERENCE TO RELATED APPLICATIONS

This application is a continuation-in-part of International Application No. PCT/GB2006/002800, filed on Jul. 27, 2006, which claims benefit of British Application No., 0516397.7, filed Aug. 10, 2005, and of British Application No. 0515521.3, filed on Jul. 28, 2005. Each of these applications is incorporated herein by reference, in its entirety, for all purposes.

FIELD OF THE INVENTION

This invention relates to new uses for exine shells of naturally occurring spores, as antioxidants and as delivery vehicles with antioxidant properties.

BACKGROUND TO THE INVENTION

Many active substances, for example pharmaceutically and nutraceutically active substances and food ingredients, are susceptible to oxidation on exposure to the air or to dissolved oxygen for instance in a humid or aqueous environment. For many, the oxidation process is induced by (ie, either initiated or accelerated by) exposure to UV radiation such as from natural daylight. Lipids such as oils tend to be particularly readily oxidised.

This susceptibility reduces the stability of the active substance and of any composition containing it. This can lead to reduced efficacy and/or to the generation of undesirable by-products which can for example spoil the flavour of a food product (eg, when fats and oils turn rancid), increase the toxicity of a drug formulation, compromise the appearance of a cosmetic product, cause operating problems for a fuel within an engine, or more generally impair performance during use.

Active substances can be protected from environmental influences such as oxygen and UV light by encapsulating them in suitable delivery vehicles. The preparation of such active-loaded delivery systems can often be complex, time consuming and expensive however. Problems can arise in ensuring that the encapsulating entities are sufficiently uniform in size and shape to ensure the resultant formulation meets quality control and regulatory standards and to provide homogeneity in active substance concentration. It can also be difficult to achieve adequately high active substance loadings in the encapsulating entities, without making those entities relatively large in size and in turn compromising the physical properties of the overall formulation.

It is moreover necessary to ensure that any encapsulated substances can be released to an adequate extent at the point of intended use. This is not always straightforward if the substance is also to be sufficiently well encapsulated as to protect it prior to use.

It is an object of the present invention to provide ways of formulating active substances which can improve their stability to oxidation and hence overcome or at least mitigate the above described problems.

STATEMENTS OF THE INVENTION

According to a first aspect of the present invention there is provided the use of an exine shell of a naturally occurring spore, or a fragment thereof, as an antioxidant.

"Naturally occurring" means that the spore is produced by a living organism, whether prokaryote or eukaryote and whether plant or animal. The spore (which term includes pollen grains and also endospores of organisms such as bacteria) may for instance be derived from a plant, or in cases from a fungus, alga or bacterium or other micro-organism.

An exine shell of a spore is the outer coating from around the naturally occurring ("raw") spore. It can be isolated from the spore by successive treatments with organic solvents, alkali and acid so as to remove the other components of the spore such as the cellulosic intine layer and lipid, protein and nucleic acid components that may be attached to or contained within the exine shell. Enzymic methods have also been used to isolate exine coatings from spores.

The resulting exine shell, which takes the form of an essentially hollow capsule, typically contains sporopollenin, a substance which is known to be chemically and physically extremely stable (G. Shaw, "The Chemistry of Sporopollenin" in *Sporopollenin*, J. Brooks, M. Muir, P. Van Gijzel and G. Shaw (Eds), Academic Press, London and New York, 1971, 305-348) but which is also inert and non-toxic.

An exine shell may be obtained from a spore in known manner, for example by harsh treatment (eg, reflux) of the spore with a combination of organic solvent and strong acid and alkali. Suitable such methods are described for instance in WO-2005/000280 (see page 10) and in the examples below. Other less severe methods may also be employed, for instance enzyme treatment (S. Gubatz, M. Rittscher, A. Meuter, A. Nagler, R. Wiermann, Grana, Suppl. 1 (1993) 12-17; K. Schultze Osthoff, R. Wiermann, J. Plant Physiol., 131 (1987) 5-15; F. Ahlers, J. Lambert, R. Wiermann, Z. Naturforsch., 54c (1999) 492-495; C. Jungfermann, F. Ahlers, M. Grote, S. Gubatz, S. Steuernagel, I. Thom, G. Wetzels and R. Wiermann, J. Plant Physiol., 151 (1997) 513-519). Alternatively, high pressure may be used to press out the internal contents of a spore through the naturally occurring pores in its outer exine layer. These methods may be used to remove proteins or carbohydrates to obtain the exine shell that retains the largely intact morphology of the original spore.

For *Lycopodium clavatum*, for example, the resultant exine shell may consist entirely or essentially of sporopollenin, optionally with a minor proportion of other materials such as chitin, glucans and/or mannans. The majority of the protein from the original spore will have been removed.

It is known from WO-2005/000280 to use spore-derived exine shells as delivery vehicles for drugs and dietetic substances. The active substance is either chemically or physically bound to, or encapsulated within, the exine shell. Reference is made in that document to the ability of the exine shells to provide a physical barrier between an encapsulated active substance and for example atmospheric oxygen, or against photolytic degradation.

However it has now surprisingly been found that an exine shell of a naturally occurring spore can itself act as an anti-oxidant to protect substances, in particular lipids and lipid-like substances, against oxidation. When oxygen is bubbled through an oil, for example, it rapidly becomes rancid as a result of oxidation processes. Yet when the oil is encapsulated within a spore-derived exine shell, it is much slower to oxidise, as shown in the examples below.

This antioxidant effect is not merely due to the shell providing a physical barrier against the ingress of oxygen, since it can be observed even when a substance is outside of, though ideally still in contact with or in a mixture with, the exine shell. Moreover it is already known that spore-derived exine shells are at least partially porous, having micropores through which lipids, proteins, nucleic acids and carbohydrates can be removed during isolation of the exine layer and through which active substances may pass when impregnating the shells, as described in WO-2005/000280. These pores would be expected to allow ambient oxygen to contact any substance encapsulated within the shell, yet in fact it has been found that even if oxygen is able to pass through the pores, oxidation of the encapsulated substance is still inhibited.

It appears therefore that the exine shell itself, or at least its surface, is capable of acting as an antioxidant. Thus in the context of the present invention, use as an antioxidant means use to increase the inherent resistance of a substance or composition to oxidation. It is not intended to encompass mere physical protection against contact with oxygen, although such protection may accompany the antioxidant effect provided by the invention.

According to the present invention, the exine shell may be derived from any suitable naturally occurring spore, whether plant or animal in origin. In this context, the term "plant" is to be construed in its broadest sense, and embraces for example mosses, fungi, algae, gymnosperms, angiosperms and pteridosperms. Moreover the term "spore" is used to encompass not only true spores such as are produced by ferns, mosses and fungi, but also pollen grains, as are produced by seed-bearing plants (spermatophytes) and also endospores of organisms such as bacteria.

Suitable species from which such spores may be obtained include the following, the diameters of their spores being shown in the second column:

| Species | Diameter |
|---|---|
| Bacillus subtilis | 1.2 μm |
| Myosotis ("forget-me-not") | 2.4-5 μm |
| Aspergillus niger | 4 μm |
| Penicillium | 3-5 μm |
| Cantharellus minor | 4-6 μm |
| Ganomerma | 5-6.5 μm |
| Agrocybe | 10-14 μm |
| Urtica dioica | 10-12 μm |
| Periconia | 16-18 μm |
| Epicoccum | 20 μm |
| Lycopodium clavatum | 25 μm |
| Lycopodium clavatum | 40 μm |
| Abies | 125 μm |
| Cucurbitapapo | 200 μm |
| Cuburbita | 250 μm. |

The exine shell used in the present invention may be of a type described in WO-2005/000280, in particular at pages 4, 8 and 9 and in Example 1. Other spores from which exine shells can be extracted are disclosed in the publications referred to at page 8 of WO-2005/000280.

According to the invention, the exine shell may be used to increase the oxidative stability of a substance to which it is added or a composition (which includes a formulation) in which it is used. It may therefore be used to reduce the oxidation rate of the substance or composition.

The exine shell may be used to protect a substance or composition against UV-induced oxidation. Again this is not intended to mean mere physical protection (ie, screening) from UV radiation. Rather, it has been found that exine shells of naturally occurring spores can be capable of reducing the tendency of a substance to oxidise in the presence of UV radiation, even though the inherent sun screening capability of such shells has been found to be relatively low. (For example, the sporopollenin of exine shells from $Lycopodium$ $clavatum$ and $Ambrosia$ $trifida$ has an approximately flat spectrum over the wavelength range 190-900 nm, the absolute value of the extinction coefficient being $1-2\times10^5$ $m^{-1}$ and not significantly different for the two types of shells. A single exine shell transmits approximately 45% of light at 450 nm. The transmission of wavelengths between 190 and 900 nm is similar (Stephen L. Atkin, Sylvain Barrier, Zhengang Cui, Paul D. I. Fletcher, Grahame Mackenzie and Vincent Panel, unpublished work).)

In accordance with the invention, the exine shell will suitably be used as an antioxidant in a formulation containing an active substance. The active substance may be encapsulated within, or chemically or physically bound to, the exine shell. Thus the exine shell may be used as a delivery vehicle for a substance. Alternatively the active substance and exine shell may be present as a simple physical mixture in the formulation.

Because of its inherent non-toxicity, a spore-derived exine shell can be particularly suitable for use as a delivery vehicle in the context of formulations which are likely to come into contact with, or be ingested by, the human or animal body. The proteinaceous materials which can otherwise cause allergic reactions to pollens are preferably removed during the processes used to isolate the exine component.

Sporopollenin, a major component of many exine shells, is one of the most resistant naturally occurring organic materials known to man, and can survive very harsh conditions of pressure, temperature and pH as well as being insoluble in most organic solvents. This too makes it highly suitable for use as a delivery vehicle.

Further potential advantages to using spore-derived exine shells as delivery vehicles, in addition to their antioxidant activity, include:

The shells can be very effective at protecting an encapsulated substance from atmospheric effects, in particular from light and/or oxygen, and therefore from premature degradation.

The physical protection they provide can help reduce loss of the substance by for instance evaporation, diffusion or leaching.

The exine shells prepared from any given organism are very uniform in size, shape and surface properties, unlike typical synthetic encapsulating entities.

There is however significant variation in spore size and shape between different species, allowing a formulation to be tailored dependent on the nature and desired concentration of the active substance, the site and manner of its intended application, the desired active release rate, the likely storage conditions prior to use, etc. . . . .

It can also be possible to encapsulate relatively high quantities of an active substance within even a small exine shell. The combination of high active loadings, small encapsulant size and adequate protective encapsulation is something which can be difficult to achieve using other known encapsulation techniques.

The ready, and often inexpensive, availability of spore exines, together with their natural origin, also make them highly suitable candidates for active substance delivery vehicles.

Further advantages associated with the use of spore-derived exine shells may be as described in WO-2005/000280, for example at pages 3 and 4 and in the paragraph spanning pages 5 and 6.

Where the exine shell is used in a formulation containing an active substance, the formulation may be suitable and/or adapted and/or intended for delivery in any manner. For example where the active substance is for systemic use (such as a pharmaceutically or nutraceutically active substance, a foodstuff or any other active substance intended to be taken into a living body, whether plant or animal), the formulation may be suitable and/or adapted and/or intended for oral, intravenous, pulmonary, nasal, transdermal, subcutaneous, buccal, intraperitoneal or any other suitable form of delivery.

The formulation may be for suitable and/or adapted and/or intended for topical delivery of an active substance to a surface, in which case the surface may be a living surface (again, either plant or animal) or an inanimate surface. The ability of the exine shell to act as an antioxidant, and not merely as a physical barrier protecting an encapsulated active substance, can be of particular significance in this context, since on release of the active substance onto a surface, the substance will then be exposed on the outside of the exine shell, yet can continue to benefit from a degree of oxidative protection.

In the context of the present invention a "topical" formulation may be suitable and/or adapted and/or intended for topical application to areas of a living body such as the skin or other epithelia, the hair, the nails or the teeth, in particular to the skin. A living surface may be either plant or animal, in particular animal, and in the case of an animal surface may either be human or non-human, in particular human.

The formulation in which the exine shell is used may have any suitable physical form. Exine shells may be present in suspension in a suitable liquid (the term "suspension" including emulsions and other multi-phase dispersions), or as a solid such as a powder or tablet. A formulation suitable for topical delivery may take the form of a lotion, cream, ointment, paste, gel, foam or any other physical form known for topical administration, including for instance a formulation which is, or may be, applied to a carrier such as a sponge, swab, brush, tissue, skin patch, dressing or dental fibre to facilitate its topical administration. It may take the form of a nasal spray or of eye or ear drops. Alternatively a topical formulation may take the form of a powder, for example when the active substance is a makeup product such as a blusher, eye shadow or foundation colour, or when it is intended for use in a dusting powder. Exine shells can be extremely efficient at absorbing liquids, in particular lipids, to result in an effectively dry product with all of the liquid encapsulated within the shells, as demonstrated in Example 11 below. Other active substances, for example food supplements or ingredients, or pharmaceutically or nutraceutically active substances, may also be formulated as powders.

Other suitable pharmaceutical and dietetic dosage forms are those disclosed in WO-2005/000280, for instance at pages 3 and 6 to 9.

An active substance may be any substance capable of producing an effect at the site of application. It may for example be selected from pharmaceutically and nutraceutically active substances, foods and food ingredients, food supplements, herbicides, pesticides and pest control agents, plant treatment agents such as growth regulators, antimicrobially active substances, cosmetics (including fragrances), toiletries, disinfectants, detergents and other cleaning agents, adhesives, diagnostic agents, dyes and inks, fuels, explosives, propellants and photographic materials. In general, the present invention may be used to stabilise any active substance, including for example oligomeric or polymeric active substances.

In one embodiment of the invention, the active substance is a cosmetic substance. A cosmetic substance may for example be selected from makeup products (for example foundations, powders, blushers, eye shadows, eye and lip liners, lipsticks, other skin colourings and skin paints), skin care products (for example cleansers, moisturisers, emollients, skin tonics and fresheners, exfoliating agents and rough skin removers), fragrances, perfume products, sunscreens and other UV protective agents, self tanning agents, after-sun agents, anti-ageing agents and anti-wrinkle agents, skin lightening agents, topical insect repellants, hair removing agents, hair restoring agents and nail care products such as nail polishes or polish removers. A perfume product may comprise more than one fragrance.

In another embodiment of the invention, the active substance may be for use in a toiletry product. It may therefore be selected from soaps; detergents and other surfactants; deodorants and antiperspirants; lubricants; fragrances; perfume products; dusting powders and talcum powders; hair care products such as shampoos, conditioners and hair dyes; and oral and dental care products such as toothpastes, mouth washes and breath fresheners.

In yet another embodiment of the invention, the active substance is for use in a household product. It may for example be selected from disinfectants and other antimicrobial agents, fragrances, perfume products, air fresheners, insect and other pest repellants, pesticides, laundry products (eg, washing and conditioning agents), fabric treatment agents (including dyes), cleaning agents, UV protective agents, paints and varnishes.

In a further embodiment of the invention, the active substance is a pharmaceutically or nutraceutically active substance, which includes substances for veterinary use. Pharmaceutically active substances suitable for topical delivery may for example be selected from substances for use in treating skin or skin structure conditions (for example acne, psoriasis or eczema), wound or burn healing agents, anti-inflammatory agents, anti-irritants, antimicrobial agents (which can include antifungal and antibacterial agents), vitamins, vasodilators, topically effective antibiotics and antiseptics.

A pharmaceutically or nutraceutically active substance may be suitable and/or intended for either therapeutic or prophylactic use.

In yet another embodiment of the invention, the active substance is a foodstuff, which includes food ingredients. Food ingredients may include for example food supplements (such as vitamins and minerals, folic acid, omega-3 oils or fibre), flavourings, fragrances, colourings, preservatives, stabilisers, emulsifiers or agents for altering the texture or consistency of a food product.

In particular the active substance may be selected from pharmaceutically and nutraceutically active substances, foodstuffs and cosmetic and toiletry substances.

In one embodiment of the invention, the active substance may be intended and/or adapted and/or suitable for topical delivery, in which case it is preferably not a substance which is intended for and/or capable of systemic use (in particular by transdermal delivery). Suitably such a substance is not intended and/or adapted and/or suitable for ingestion, in particular by humans.

In certain cases it may be suitable for the active substance to be a substance other than an essential oil, or at least for it not to be an essential oil which is intended and/or suitable for systemic use in a living body.

In some cases it may be suitable for the active substance to be a substance other than a drug (at least a drug which is intended and/or suitable for systemic delivery) or a dietetic substance.

In some cases it may be suitable for the active substance to be a substance other than a vitamin, a mineral, an essential oil, a food flavouring and/or a nutraceutical.

The active substance may comprise a volatile substance, in particular a fragrance. The present invention can be particularly suitable for formulations containing such substances as the exine shell can help to inhibit release of any volatile components prior to use. This is also not necessarily predictable, bearing in mind that exine shells of naturally occurring spores are known to be porous. Nevertheless, they can in cases be capable of encapsulating volatile actives and reducing their loss to the atmosphere, as shown in Example 10 below.

The active substance may be a lipid or lipid-like substance (for example, an oil, fat or wax), and/or it may be lipophilic. It may be present in a secondary fluid vehicle such as a liquid vehicle, in particular a non-aqueous (or essentially or at least partially non-aqueous) vehicle, more particularly a non-aqueous vehicle and yet more particularly a lipid vehicle, such as an oil. The active substance may therefore be present in the form of a solution or suspension, the term "suspension" including emulsions and other multi-phase dispersions. A secondary vehicle may for example be a water-in-oil or oil-in-water-in-oil emulsion.

The active substance may itself be a naturally occurring substance or derived from a natural source, in particular a plant source.

In some cases the active substance may be non-polar.

The active substance may be sensitive to one or more external influences such as heat, light, oxygen or water. In particular it may be susceptible to oxidation, in particular from atmospheric or dissolved oxygen. It may be susceptible to UV-induced oxidation (ie, photochemical oxidation), more particularly under ambient conditions.

The formulation containing the active substance may be suitable and/or adapted and/or intended for storage and/or use in a fluid environment which contains oxygen, for instance in air or in a liquid such as water which contains dissolved oxygen. It may be suitable and/or adapted and/or intended for storage and/or use in an environment which is or may be exposed to UV radiation, in particular from sunlight. In these contexts the present invention can be particularly effective in protecting the active substance against oxidation and therefore in increasing the stability of the overall formulation.

A formulation in which the present invention is used may contain more than one active substance. Two or more such substances may for example be co-encapsulated in the same exine shell. Instead or in addition, a formulation prepared according to the invention may comprise two or more populations of active substance-containing exine shells, each chemically or physically bound to, or encapsulating, a different active substance.

Thus for example, a cosmetic formulation prepared according to the invention might contain both a sunscreen and an insect repellant, or a sunscreen and a moisturiser, or a foundation or other skin colouring agent and a sunscreen. Two or more active substances may therefore benefit from the antioxidant protection afforded by the exine shell(s).

This can also enable two or more active substances to be kept separate prior to use—of value for example if they are incompatible with one another or would interact in an undesirable manner—and then released together in situ at the intended point of use.

A formulation prepared according to the invention may be contained in a product, which may for example be selected from cosmetic products; toiletries (eg, bath products, soaps and personal care products); hair care products; nail care products; dental products such as toothpastes, mouth washes and dental flosses; household products (whether for internal or external use) such as surface cleaners, disinfectants, air fresheners, pest repellants and laundry and fabric treatment products; paints, inks, dyes and other colouring products; adhesive products; pharmaceutical and nutraceutical products; food products, including food additives and food ingredients; agricultural and horticultural products; fuels; explosives; propellants; and photographic materials.

Such a product may be suitable and/or adapted and/or intended for delivery by any suitable route, including for instance by topical application.

In particular such a product may be selected from cosmetic products (which includes skin care products), toiletries, hair and nail care products and dental products.

In another embodiment of the invention, the product is a pharmaceutical or nutraceutical product, which in both contexts includes products for veterinary use.

In yet another embodiment, the product is a food product.

In a formulation prepared according to the invention, the active substance may be chemically or physically bound to, or encapsulated within, the exine shell. Suitably it is either physically bound to or encapsulated within the exine shell. More suitably it is at least partially encapsulated within the shell.

Suitable ways in which a substance may be chemically bound to an exine shell are described in WO-2005/000280, for example in the paragraph spanning pages 4 and 5, and at pages 14 to 22 and 24 to 32. They may involve chemical derivatisation of the exine shell so as to facilitate its chemical binding to the substance in question. Chemical binding may encompass covalent or other forms of chemical bond, for example hydrogen bonds, sulphide linkages, Van der Waals bonds or dative bonds.

Physical binding of an active substance to an exine shell may include for example adsorption (eg, involving hydrophobic/hydrophilic interactions) of the substance onto a surface (whether internal or external) of the shell.

Encapsulation of an active substance means that the substance is retained within the cavities that are inherently present in the exine shell wall and/or within the central cavity defined by the exine shell.

An active substance may be attached to an exine shell by more than one of the above described means; for example, it may be encapsulated within the shell and also chemically bound to it, or a portion of the substance may be adsorbed onto the outer surface of the shell whilst another portion is contained inside the shell.

In a formulation prepared according to the invention, the exine shell may have a diameter (which may be determined by scanning electron microscopy) of from 1 to 300 µm, suitably from 1 to 250 µm or from 3 to 50 µm or from 15 to 40 µm. Grass pollen-derived exines, and other exine shells of approximately 20 µm diameter, might also be expected to be suitable.

The preferred exine particle size may depend on the intended mode of administration of the relevant active substance or formulation. For example, for pulmonary delivery relatively small particles (for instance of diameter 10 µm or less, or 8 or 5 µm or less for nasal delivery or less than 5 µm for delivery into the lungs) may be preferred. For oral delivery, particle sizes of less than 25 µm may be suitable. However, if the active substance is intended for delivery to the gut (for example certain nutraceuticals, such as probiotics) then particle sizes of 40 µm or greater may be suitable. In general, for active substances intended for systemic use, particle sizes of 25 µm or less may be preferred because of their ready ability to pass into the bloodstream.

In some cases larger exine shells, for example of 30 or 40 µm diameter or greater, may be particularly suited as topical delivery agents as they are less likely to be persorbed into the bloodstream. If however a topically delivered active substance is required to penetrate the hair follicles, then smaller exine shells—for example of 7 µm or less, or 5 or 3 µm or less, or ideally 2 µm or less such as from 1 to 2 µm—may be suitable.

Larger exine shells may have the advantage of allowing higher active substance loadings, but may compromise the texture and/or appearance of the overall formulation, which for oral or topical delivery may be of significance. Thus in such contexts, in particular for oral delivery of for example pharmaceutical or nutraceutical substances or foods, it may be suitable for the exine shells to have a diameter of 10 μm or less. Moreover when using larger shells, an associated active substance may be less homogeneously distributed throughout a formulation than when associated with a larger number of smaller shells. In general a minimum diameter of 4 μm might be preferable so as to be able to achieve reasonable active substance loadings. However there may be cases where the minimum diameter is suitably 60 μm or even more.

In one embodiment of the invention, the exine shell may additionally contain all or part of the cellulose intine layer from the naturally occurring spore. This can be achieved if the spore is subjected to treatment with only organic solvent and alkali, and not with acid. Such base hydrolysis, for instance using potassium hydroxide, can ensure that proteinaceous components of the spore are removed, yet can allow at least a proportion of the original cellulosic intine to survive.

In one embodiment of the invention, the exine shell may be intact or substantially so. In other words, apart from the micro- or nanopores which are naturally present in the surfaces of such shells, it will provide a continuous outer wall defining an inner cavity into which an active substance can be loaded. The exine shell may however be broken or damaged in parts; the invention thus embraces the use of a fragment of a spore-derived exine shell, in particular in the case where an active substance is chemically or physically bound to the exine shell. Suitably however the exine shell is continuous over at least 50%, suitably at least 75 or 80 or 90%, of the surface area which an exine shell from the relevant species would have if intact. Thus in many cases, the present invention relates to the use of an exine shell of a naturally occurring spore rather than to a fragment of such a shell.

The exine shell may be chemically modified, either to alter its properties (for example its solubility) or to target it to an intended site of administration (for example, to render it more surface-active), or to facilitate its attachment to an active substance. Suitable such chemical modifications, and methods for achieving them, are described in WO-2005/000280, in particular in the paragraph spanning pages 4 and 5 and at pages 14 to 22 and 24 to 32. The outside of the exine shell may for instance be modified by the (typically chemical) attachment of functional groups such as cationic and/or anionic groups (see WO-2005/000280 and also G. Shaw, M. Sykes, R. W. Humble, G. Mackenzie, D. Marsdan & E. Phelivan, *Reactive Polymers,* 1988, 9, 211-217), and/or functional groups which increase the affinity of the shell for a surface to which it is intended to be applied.

An active substance may be attached to, or encapsulated within, an exine shell using known techniques, again suitably as described in WO-2005/000280. In particular an exine shell may be impregnated with an active substance by immersing the shell in the active substance or a solution or suspension thereof. One or more penetration enhancing agents may be used, again as described in WO-2005/000280, to aid impregnation of the shell by the active substance. A reduced or increased pressure (with respect to atmospheric pressure) may instead or in addition be used to facilitate impregnation.

The exine shell may be loaded with any suitable quantity of the active substance, depending on the context of intended use. A formulation prepared according to the invention may for example contain the active substance and exine shells at an active substance:exine shell weight ratio of from 0.01:1 to 35:1 or 33:1, such as from 0.01 to 20:1 or from 0.1:1 to 12:1 or 8:1 or 5:1, or from 0.5:1 to 5:1, or from 1:1 to 5:1 or 8:1. The loading achievable may depend on the size of the exine shell, if at least partial encapsulation of the active substance is intended.

In accordance with the invention, a formulation may contain a proportion of an active substance which is not encapsulated within the inner cavity of the exine shell, since the exine shell may still contribute an antioxidant effect even when the substance is outside the shell. Thus relatively high active substance concentrations may be used in the formulation, for example active substance:exine shell weight ratios in excess of 5:1 or 10:1 or even 20:1 or 30:1. Again the maximum suitable loading may depend on the size of the exine shell.

In cases, the weight ratio of the active substance to the exine shell in the formulation is such that the exine shell is filled with the active substance (or with an active substance-containing solution or suspension) and in addition there is a coating of 10 μm thickness or less of the active substance/solution/suspension around the outer surface of the shell. This situation may represent a suitable maximum for the active substance to exine shell weight ratio, allowing a reasonable level of antioxidant effect from the exine shell.

The exine shell may be coated with a barrier layer for further protection of an associated active substance against atmospheric effects. This may be of particular use for the delivery of volatile active substances, and/or oxygen sensitive substances. Suitable coatings are solid or semi-solid under the normal storage conditions for the formulation (typically at room temperature) but may melt at a higher temperature (for instance, skin temperature) at which they are intended to be topically applied. Lipid coatings may be suitable for use in this way, examples including butters and other solid fats (eg, cocoa butter or hardened palm kernel oil), oils (eg, cod liver oil) and waxes (eg, carnuba wax or beeswax). In particular if an active substance is intended for topical delivery, the coating may be a material which melts at or around skin temperature (cocoa butter is an example of such a material), and can therefore allow release of the active substance on topical application to the skin. Other potential coatings may be materials which can rupture on application of manual pressure, for example brittle solids such as shellac, or other materials which melt, break or otherwise change on administration (eg, topically) so as to allow release of the active substance. Gelatin may for example be a suitable coating material.

Other known coating excipients may be chosen depending on the desired delivery route and intended site of action (for example, coatings may be used to delay, target or otherwise control release of an active substance). Various natural or synthetic coating excipients, including oligomers and polymers, may be used to protect the active substance in a formulation prepared according to the invention. Vegetable-derived coating materials may be preferred.

Coatings may be applied to exine shells in known fashion, for instance by spraying, rolling, panning or dipping. Coatings do not necessarily have to be continuous around the entire outer surfaces of the shells.

A second aspect of the present invention provides the use of an exine shell of a naturally occurring spore, or a fragment thereof, for the purpose of removing a previously formed oxidation product from a substance or composition. In other words, it has been found possible to "clean up" a substance or composition which has already undergone a degree of oxidation, removing at least some of the products of that oxidation and thereby improving the effective stability of the substance or composition. For example, where the substance is a lipid such as an oil, and has already turned at least partially rancid, an exine shell of a spore may be added to that substance, and/or may be loaded with that substance, in order to reduce its rancidity.

The second aspect of the invention therefore embraces a method for reducing rancidity, or other oxidative degradation, of a substance or composition, the method involving encapsulating the substance or composition in, or chemically or physically binding it to, or in cases mixing it with, an exine shell of a naturally occurring spore or a fragment thereof.

Thus the second aspect of the invention may be carried out for example by encapsulating an at least partially oxidised active substance or composition in an exine shell of a naturally occurring spore, or chemically or physically binding the active substance or composition to the exine shell or fragment. On subsequent separation of the substance or composition from the exine shell, for example on delivery to an intended site of action, it may then be found to be less oxidised than prior to being associated with the exine shell. The degree of oxidation in such cases may be measured in any suitable manner, for instance by assessing the level of by-products of oxidation reactions (peroxides, for example, and/or acids) in the active substance or composition. In the case of a lipid active substance, the degree of oxidation will typically equate to the level of rancidity.

In an embodiment of the second aspect of the invention, it may be preferred for the exine shell or fragment to contain all or part of the cellulose intine layer from the naturally occurring spore. This can be achieved, as described above, if the spore is subjected to treatment with only organic solvent and alkali, and not with acid.

It may be suitable, in accordance with the second aspect of the invention, for the exine shell to have a particle diameter of from 20 to 60 μm or from 20 to 50 or 30 to 50 μm, such as around 40 μm. The exine shell may be derived from *Lycopodium clavatum* spores.

A third aspect of the invention provides a method for protecting an active substance from oxidation, and/or for increasing the stability of the active substance or of a composition containing it, the method involving formulating the active substance with an exine shell of a naturally occurring spore or a fragment thereof. Suitably the active substance is encapsulated within, or chemically or physically bound to, the exine shell or fragment.

A fourth aspect of the invention provides a method for formulating an active substance, the method involving (a) preparing or providing an exine shell of a naturally occurring spore or a fragment thereof; and (b) encapsulating the active substance in the shell, or chemically or physically binding the active substance to the shell or fragment, for the purpose of providing an antioxidant effect in the resultant formulation.

A fifth aspect of the invention provides an exine shell of a naturally occurring spore, or a fragment thereof, for use as a pharmaceutically active antioxidant.

A sixth aspect provides the use of an exine shell of a naturally occurring spore, or a fragment thereof, in the manufacture of a medicament for delivering an antioxidant to a human or animal body.

A seventh aspect provides a method of treatment of a human or animal patient in need of an antioxidant, the method involving administering to the patient a therapeutically (which includes prophylactically) effective amount of an exine shell of a naturally occurring spore or a fragment thereof.

In accordance with the fifth to the seventh aspects of the invention, the exine shell or fragment may be administered together with another pharmaceutically active substance, for example a lipid lowering agent such as a statin. It may be used to treat any condition which is caused or exacerbated by oxidative stress, for example cardiovascular disease. It may be used to treat any condition which is caused or exacerbated by the generation in the body of free radicals and/or other oxidants, for example from ingested materials; it may thus be used for instance to reduce inflammation and/or to treat cancers such as bowel cancer.

Since a spore-derived exine shell may be resistant to high levels of moisture, acid, alkali and heat, it will not typically dissolve or decompose in the mouth. It is also tasteless. It can therefore be used to mask the flavour of an active substance, for example a pharmaceutical or nutraceutical, a foodstuff or a food supplement.

Thus an eighth aspect of the invention provides the use of an exine shell of a naturally occurring spore, or a fragment thereof, as a taste masking agent. Again the exine shell or fragment will suitably be used as part of a formulation containing an active substance, in order to mask, at least partially, the flavour of the active substance. The formulation may be suitable and/or adapted and/or intended for oral delivery, or for delivery by any other route which might result in a perception of flavour for a patient to whom it was administered.

A further aspect of the present invention provides a method for preparing an active substance-containing formulation, and/or a method for formulating an active substance to have improved oxidative stability, and/or a method for improving the oxidative stability of an active substance, the method involving the steps of obtaining an exine shell of a naturally occurring spore, or a fragment thereof; mixing the active substance with the exine shell or fragment; and measuring the oxidative stability of the mixture of the active substance with the exine shell or fragment. The oxidative stability measurement may be used to confirm that the thus-formulated active substance has a desired minimum level of oxidative stability.

Such a method may involve the steps of obtaining an exine shell of a naturally occurring spore, or a fragment thereof; measuring the oxidative stability of the active substance in the absence of the exine shell or fragment so as to obtain a first oxidative stability value; mixing the active substance with the exine shell or fragment; and measuring the oxidative stability of the mixture of the active substance with the exine shell or fragment so as to obtain a second oxidative stability value. In this case the second oxidative stability value is preferably higher than the first, i.e. the active substance has a higher oxidative stability after mixing with the exine shell or fragment.

The oxidative stability of an active substance (or of a formulation containing the substance) may generally be defined as the resistance which the substance or formulation exhibits to degradation caused by exposure to oxygen, typically in the presence of an oxidation initiator such as UV light, heat or free radicals. It may be defined as the rate of change, with time, in a property of the substance or formulation, on exposure to oxygen (typically atmospheric oxygen). The change may therefore be caused by (which includes initiated and/or exacerbated and/or speeded by) oxygen. The change may be caused by (which includes initiated and/or exacerbated and/or speeded by) exposure to UV radiation as well as oxygen.

The property of the active substance which changes due to oxidation may for example be selected from the chemical structure of the substance; its purity; a physical property such as viscosity or electrical or thermal conductivity; the activity of the substance (which includes biological and/or pharmacological activity); its bioavailability on administration to a living subject; the taste, smell or appearance (in particular the colour) of the substance; and its shelf life (i.e. the period of time for which it can be stored before its activity and/or another property cease to fall within a predetermined specification). In particular the property may be a chemical property; it may for instance involve a change in the molecular structure of the active substance, converting it for example into an oxidised form of the original molecule, or in the morphology of the substance. The generation of an oxidised form of the active substance would also generally serve to reduce its purity, and typically also to alter properties such as activity, taste and smell. The property may be the content, in an active substance-containing formulation, of a (typically undesired) oxidation product (i.e. a product derived by oxidation of the active substance). Thus for example, the property may be the free fatty acid content of a lipid active substance or lipid-containing formulation, and/or the peroxide value of such a substance or formulation.

In an embodiment of the invention, in particular in the case of a lipid active substance, for example an oil, or of a nutraceutical active substance or a foodstuff or food or beverage ingredient, the property may be selected from the taste, smell and colour of the active substance, in particular the taste and smell.

In an embodiment of the invention, in particular in the case of a lipid active substance such as an oil, the property may be selected from the peroxide value and the free fatty acid content of the substance, in particular the peroxide value.

Oxidative stability may thus be measured, in accordance with the invention, by measuring the rate of change in a parameter such as peroxide value, for instance as in the experimental examples below. Additionally or alternatively, oxidative stability may be measured by measuring the rate of change of redox potential, thiobarbituric acid value, iodine value, anisidine value, TOTOX value (defined as two times the peroxide value added to the anisidine value) and/or free fatty acid content, and/or by the RANCIMAT, active oxygen or Schaal oven test methods, or by any other suitable test method.

A yet further aspect of the invention provides a method for marketing an active substance, or a formulation containing an active substance, the method involving the steps of obtaining an exine shell of a naturally occurring spore, or a fragment thereof; mixing the active substance with the exine shell or fragment, or adding the exine shell or fragment to the formulation, so as to increase the oxidative stability of the active substance or formulation; and marketing the resultant mixture or formulation together with information regarding its improved oxidative stability and/or shelf life.

The term "marketing" is used herein to refer to any type of offer to sell and/or any activity designed to promote sales. The marketing of a an active substance, composition, or formulation of the invention with an indication that the active substance, composition, or formulation has been tested to assure oxidative stability and/or any property affected by oxidative stability can include, for example: enclosing the active substance, composition, or formulation in a container or package that includes such a stability indication; packaging the substance, composition, or formulation with a package insert that includes the stability indication; providing the stability indication in a publication that describes the formulation (e.g., publication can be via printed publications such as newspapers, magazines, pamphlets, etc., as well as publication via the internet); providing the stability indication in a commercial aired on the radio, television, or the internet.

In the context of the present invention, "mixing" an exine shell or fragment with an active substance may at its simplest involving simply contacting the exine shell or fragment with the active substance, for instance by introducing the exine shell or fragment into the active substance or into a formulation containing it. The mixing may involve a physical and/or a chemical interaction between the active substance and the exine shell or fragment: for example, the active substance may be encapsulated within, or chemically or physically bound to, the exine shell or fragment, for instance as described above.

In an embodiment, the exine shell or fragment may be in contact with only a proportion of a quantity of an active substance or active substance-containing formulation. Thus, exine shells or fragments need not for example be distributed throughout a fluid active substance or formulation, but can merely be present at a location within the fluid, the natural movement of molecules in the fluid (for instance, due to Brownian motion or convection currents) helping effectively to distribute the antioxidant effect of the exine shells or fragments throughout the system.

Another aspect of the present invention provides a method for removing a previously formed oxidation product from an active substance or formulation, the method involving selecting an active substance, or a formulation containing an active substance, which has already undergone at least some oxidative degradation; selecting an exine shell of a naturally occurring spore, or a fragment thereof; and mixing the exine shell or fragment with the active substance, or adding it to the formulation.

This method may additionally involve subsequently separating the active substance or formulation from the exine shell or fragment. The method may be used for example to reduce the rancidity of a lipid material such as an oil.

The method suitably involves measuring the extent to which the active substance or formulation has undergone oxidative degradation, prior to mixing or adding the exine shell or fragment; this yields a so-called "initial oxidative degradation value". It may involve measuring the degree of oxidative degradation after mixing or adding the exine shell or fragment, to yield a "final oxidative degradation value". Such measurements may for instance involving measuring the concentration of an oxidation product in the substance or formulation, which concentration will suitably be reduced by the mixing or addition of the exine shell or fragment. One or more additional oxidative degradation measurements may be taken, whether before, after and/or between the so-called "initial" and "final" values referred to above.

Also provided by the invention is a kit for use in reducing the rancidity, or other oxidative degradation, of an active substance or a formulation containing an active substance, the kit containing an exine shell of a naturally occurring spore, or a fragment thereof, together with instructions for mixing the exine shell or fragment with the active substance, or for adding it to the formulation, in order to reduce the degree of oxidative degradation of the active substance or formulation.

For use in the present invention, an exine shell or fragment thereof may consist entirely or essentially of sporopollenin, optionally with a proportion of other materials such as chitin, glucans and/or mannans. Ideally the majority of the protein from the original spore will have been removed.

Thus, for example, an exine shell or fragment may contain 2% w/w or less of nitrogen, or 1.5 or 1.2 or 1 or 0.7 or 0.6 or 0.5% w/w or less, or 0.4 or 0.3% w/w or less or 0.2 or 0.1% w/w or less, based on the total weight of the shell or fragment. In some cases the exine shell or fragment will contain no, or substantially no (for instance less than 0.01% w/w), nitrogen.

The exine shell or fragment may contain for example 95% w/w or more of sporopollenin, in cases 96 or 97 or 98 or 99% w/w or more, such as from 95 to 99% w/w, based on the total weight of the shell or fragment.

The exine shell or fragment thereof may contain 10% w/w or less of lipid materials, based on the total weight of the shell or fragment, suitably 9 or 8 or 7 or 6 or 5% w/w or less, or in cases 4 or 3 or 2 or 1% w/w or less. Such lipids might for instance include aldehydes, wax esters, fatty acids, fatty alcohols, carotenoids, flavonoids and/or phenolic conjugates, and/or those lipids listed by R. Wierman and S. Gubatz in "Pollen wall and sporopollenin", *International Review of Cytology* 1992, 140: 35-72.

The exine shell or fragment may be, or be derived from, *Lycopodium clavatum*, ryegrass, rye, Timothy grass, hemp, rape, wheat or maize pollen spores. It may be, or be contained in, lycopodium powder. It may in particular be or be derived from *Lycopodium clavatum* or ryegrass pollen spores, or used in the form of lycopodium powder. In particular it may be or be derived from *Lycopodium clavatum* spores.

In an embodiment of the invention, the exine shell or fragment may be derived from the same species and/or variety (preferably variety) of plant or other organism (in particular plant) as the active substance. Thus, for example, an exine shell or fragment derived from hemp may be used as an antioxidant in hemp oil or a hemp oil-containing formulation.

In an embodiment, the exine shell or fragment has been prepared by a process which does not result in acetylation, esterification or other derivatisation (in particular acetylation) of hydroxyl groups on constituents (in particular sporopollenin) of the exine shell or fragment. Thus, the exine shell or fragment may suitably be prepared from a naturally occurring spore by a process which does not involve acetolysis.

In accordance with the present invention, an active substance is contacted with or mixed with an exine shell of a naturally occurring spore or a fragment thereof. In the resultant mixture, the weight ratio of the active substance to the exine shell or fragment may be up to 99.95:0.05, or up to 99.9:0.1, or up to 99.8:0.2, or up to 99.7:0.3, or up to 99.6:0.4, or up to 99.5:0.5, or up to 99.2:0.8, or up to 99:1. The ratio may be up to 98.5:1.5, or up to 98:2, or up to 97:3, or up to 96:4, or up to 95:5. It may be 84:16 or greater, or 85:15 or greater, or 86:14 or greater, or 87:13 or greater, or in cases 88:12 or 89:11 or 90:10 or greater.

Thus the weight ratio of the active substance to the exine shell or fragment may be for example from 99.7:0.3 to 84:16, or from 99.5:0.5 to 84:16, or from 99.5:0.5 to 85:15. It may be from 99:1 to 85:15.

Thus a further aspect of the invention provides a formulation containing an active substance and an exine shell of a naturally occurring spore, or a fragment thereof, wherein the weight ratio of the active substance to the exine shell or fragment is from 99.9:0.01 to 84:16.

Suitably when the exine shell or fragment is contacted with the active substance at an active substance:exine/fragment weight ratio of 95:5 or lower, or in cases of 96:4 or 97:3 or 98:2 or 99:1 or even 99.5:0.5 or lower, the oxidative stability of the active substance, and/or of the formulation containing it, is improved to the extent that its rate of degradation with time (on exposure to oxygen) is 90% or less of the rate of degradation of the active substance or formulation under the same conditions but in the absence of the exine shell or fragment. For example, where the active substance is a lipid, in particular an oil, its rate of increase in peroxide value with time, on exposure to oxygen, is suitably 90% or less, in the presence of the exine shell or fragment, of the rate of increase in peroxide value of the same active substance under the same conditions but in the absence of the exine shell or fragment. Its rate of degradation may be 85% or less, or 80 or 75 or 70% or less, or 65 or 60% or less, or in cases even 50 or 40 or 35 or 30% or less, compared to the value in the absence of the exine shell or fragment.

The rate of oxidative degradation (such as increase in peroxide value) may for example be measured over a period of one week, suitably 2 or 3 or 4 or 5 weeks, or more from the point of mixing of the active substance and the exine shell or fragment. In cases it may be measured over a period of 6 or 7 or 8 or 9 or 10 weeks or more. The rate may be averaged and/or linearised over such a time period—for instance, it may be calculated by subtracting the initial amount of degradation from the final amount of degradation, and dividing the difference by the total time elapsed, and/or it may be calculated using a graph showing the change in a relevant property (such as peroxide value) with time, which may be linearised for instance using a program such as MICROSOFT EXCEL spreadsheet.

In accordance with the present invention, the active substance may in particular be selected from oils, vitamins (or vitamins other than vitamin C), flavourings (for example essential oils such as peppermint oil, fruit juices and oils, menthol, vanillin or other pharmaceutically acceptable flavourings or food flavourings), topically active drugs (for example corticosteroids), and mixtures thereof. In cases it may be selected from oils, vitamins, flavourings and mixtures thereof. It may be selected from oils, vitamins and mixtures thereof. It may be selected from topically active drugs, cosmetics, toiletries and mixtures thereof, or from topically active drugs, cosmetics and mixtures thereof. In cases it may be a topically active drug.

The active substance may be selected from pharmaceutically active substances, dietetic active substances (which includes nutraceutically active substances), foods and food ingredients and food supplements.

In an embodiment of the invention, the active substance is a foodstuff, which includes beverages and also food and beverage ingredients. Food and beverage ingredients may include for example dietary supplements (such as vitamins and minerals, folic acid, omega-3 oils, fibre or so-called "probiotics" or "prebiotics"), flavourings, fragrances, essential oils, colourings, preservatives, stabilisers, emulsifiers or agents for altering the texture or consistency of a food product. The active substance may in particular be selected from dietetic active substances, dietary supplements and mixtures thereof.

The active substance may be a lipid, for example selected from oils and fats, in particular oils. Where the active substance is an oil, it may for example be selected from sunflower oil, cod liver oil, soybean oil, echium oil, rapeseed oil, fish oil (including any component thereof, such as an omega-3 oil), olive oil, hemp oil, borage oil, canandula (French marigold) oil, linseed oil and mixtures thereof.

In an embodiment of the invention, the active substance is an oil other than sunflower oil, cod liver oil, soybean oil, echium oil, rapeseed oil, fish oil or olive oil. It may for example be selected from hemp oil, borage oil, canandula oil, linseed oil and mixtures thereof.

In an embodiment, the active substance is not thyroxine, human recombinant growth hormone, insulin, sunflower oil, glycine, copper sulphate or LR White Resin. In an embodiment, the active substance is not AZT monophosphate.

In an embodiment, the exine shell or fragment, and in particular the sporopollenin present in the spore, exine shell or fragment, is not chemically derivatised. For example, in an embodiment the exine shell or fragment does not contain an aminosporopollenin.

In an embodiment, the active substance is not a mineral, an essential oil, a cholesterol lowering agent, a vitamin, a food flavouring, a nutraceutical, a flavour, a preservative, an antioxidant, a metal or metal derivative, a peptide or genetic material, a cyclosporine, a taxane or any of the drugs referred to at page 5, second paragraph of WO-2005/000280, the entire contents of which are herein incorporated by reference.

In an embodiment, the active substance is not an image enhancing material. In an embodiment, it is not a metal complex, chelate or other derivative, as for instance referred to in WO-2006/064227, the entire contents of which are herein incorporated by reference. In an embodiment, the active substance is not a gadolinium, manganese or iron derivative. In an embodiment, the active substance is not a radionucleotide. In an embodiment, the active substance is not a copper (II) EDTA complex, silver chloride, an alginate formulation (in particular Gaviscon®) or a gadolinium complex. In an embodiment, it is not cod liver oil, sunflower oil, soybean oil, echium oil, rapeseed oil or fish oil.

In an embodiment of the invention, the exine shell or fragment is mixed with the active substance in the absence of an emulsifier, in particular an emulsifier of the type disclosed in WO-03/094942, the entire contents of which are herein incorporated by reference. In an embodiment, the exine shell or fragment is mixed with the active substance in the absence of a hydrophilic solvent, in particular a hydrophilic solvent of the type disclosed in WO-03/094942.

In an embodiment, a mixture of active substance and exine shell or fragment, prepared according to the invention, is in the form of a liquid as opposed to a solid, cream, paste or gel in which the active substance has only limited mobility. For example, such a liquid may have a kinematic viscosity at 20° C. of 5000 centipoise or lower, preferably of 4000 or 3000 or 2000 centipoise or lower, suitably of 1900 or 1800 or 1700 or 1600 or even 1500 centipoise or lower, in cases of 1400 or 1300 or 1200 or 1100 or 1000 centipoise or lower. Suitably the mixture is in the form of a fluid that is able to flow under its own weight at typical storage temperatures, for example at 25 or 23 or 20° C., and ambient pressure.

In an embodiment, the exine shell or fragment is used in a solid form, which may be suspended or otherwise dispersed in a liquid system but is not dissolved.

In an embodiment, the active substance is not MIGLYOL oil, glycerin, paraffin oil, a lecithin/glycerin cream such as LIPOID SLM 2005, an algae extract such as CAELICO or any of the active substances referred to, or exemplified, in WO-03/094942. In an embodiment, the active substance is not a heavy metal salt, in particular a lead, cadmium or arsenic (V) salt. In an embodiment, it is not a perfume or fragrance.

In an embodiment, the active substance is not glucose, citric acid, beta-carotene or vitamin C. In an embodiment, it is not a sweetener such as acesulfam K or aspartame. In an embodiment, it is not a fruit juice.

In an embodiment, the active substance is not an aqueous metal salt solution, in particular of a zinc (II), cadmium (II), aluminium (III), copper (II) or nickel (II) salt.

In an embodiment, the active substance is not ferrous sulphate, a nitrite (in particular sodium nitrite) or a mixture thereof.

In an embodiment, the active substance and the exine shell or fragment are not formulated as a pulsating release composition. In an embodiment, the mixture of active substance and exine shell or fragment does not carry a coating layer.

In an embodiment, the active substance is not a drug, in particular a drug of the type disclosed in U.S. Pat. No. 5,275,819, the entire contents of which are herein incorporated by reference. In an embodiment, the active substance is not an aromatic molecule, a flavouring, a hormone or a protein. In an embodiment, it is not insulin or angiotensin. In an embodiment, it is not insulin. In an embodiment, it is not a pheromone, in particular an insect pheromone.

In an embodiment, the active substance is not vasopressin, calcitonin, gastrin, GNRH, decapeptide Nafarelin or any of the active substances exemplified in U.S. Pat. No. 5,275,819.

In an embodiment, the active substance is not an essential oil, in particular cinnamon or clove oil. In an embodiment, it is not eugenol.

In an embodiment, the active substance is not a herbicide, larvicide, plant growth regulator, nematocide or pesticide.

In an embodiment, the active substance is not a macromolecule. In an embodiment, it is not a cell, a micro-organism or an antibody. In an embodiment, it is not a colloid. In an embodiment, it is not either ethanol or acetone. In an embodiment, it is not sugar, serum albumin or a dextran. In an embodiment, it is not olive oil, petroleum ether or diethyl ether. In an embodiment, it is not a protein. In an embodiment, it is not a detergent. In an embodiment, it is not sodium cellulose sulphate.

In an embodiment, the mixture of active substance and exine shell or fragment is not for use as a filtration or chromatography substrate.

In an embodiment, the exine shell or fragment is not derived from pine pollen. In an embodiment, the active substance is not either a biopolymer or a primer for the solid-phase synthesis of a biopolymer. In an embodiment, it is not a ligand, a sugar (in particular a dextran), a dye (in particular a low molecular weight dye, more particularly a fluorescein dye), latex particles, an alpha-methyl glucoside or a polyacrylic acid sodium salt.

In an embodiment, the active substance is not a peptide, in particular a tetrapeptide or polypeptide.

In an embodiment of the invention, the active substance and the exine shell or fragment may be combined in a food or beverage, or in an ingredient (which includes a dietary supplement) for a food or beverage. In an embodiment, they may be combined in a cosmetic formulation.

The active substance will typically be susceptible to oxidation, for instance under ambient conditions. It may be susceptible to UV-induced oxidation, thermally induced oxidation, and/or oxidation due to another factor such as enzymatic activity, ionising radiation, metal ions and/or metalloproteins.

The active substance may in particular be a material which is susceptible to oxidation, the oxidation of which results in a significant, or at least detectable, change in its taste and/or smell. Oils and other lipids are common examples of such active substances. It may be a material, for example a pharmaceutical or nutraceutical or food supplement, which suffers a reduction in its biological and/or pharmacological activity on oxidation.

Throughout the description and claims of this specification, the words "comprise" and "contain" and variations of the words, for example "comprising" and "comprises", mean "including but not limited to", and do not exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Preferred features of each aspect of the invention may be as described in connection with any of the other aspects.

Other features of the present invention will become apparent from the following examples. Generally speaking the invention extends to any novel one, or any novel combination, of the features disclosed in this specification (including any accompanying claims and drawings). Thus features, integers, characteristics, compounds, chemical moieties or groups described in conjunction with a particular aspect, embodiment or example of the invention are to be understood to be applicable to any other aspect, embodiment or example described herein unless incompatible therewith.

Moreover unless stated otherwise, any feature disclosed herein may be replaced by an alternative feature serving the same or a similar purpose.

The present invention will now be described by means of the following non-limiting examples.

EXAMPLES

The following experiments demonstrate the ability of spore-derived exine shells to act as natural antioxidants, in particular to reduce the oxidation rates of oils. This in turn shows their suitability for use as delivery vehicles for oxygen-sensitive active substances, in particular lipids, and for increasing the stability of such substances prior to, during and after administration.

The exine shells used were extracted from the spores of *Lycopodium clavatum* L. (common club moss), which can be purchased for example from Unikem, Post Apple Scientific, Fluka and Tibrewala International. Both 25 and 40 μm spores were tested, the 40 μm being derived from a sub-species or genetic variant of the plant. The former have a reticulated outer surface whilst the latter appear smoother and rounder. Both are believed to have an exine shell approximately 1.5 μm thick.

The exine shells were isolated from other components present in the spores (in particular the proteinaceous components) using the extraction procedures described below. Samples designated "AHS" were subjected to acid hydrolysis with phosphoric acid following base hydrolysis with potassium hydroxide, whereas those designated "BHS" were subjected only to base hydrolysis with potassium hydroxide. The BHS samples therefore comprised not only the exine shell but also a proportion of the cellulosic intine layer.

Firstly, the raw spores were suspended in acetone and stirred under reflux for 4 hours. For this, 250 g of the spores were dissolved in 750 ml of acetone, and refluxed for 4 hours in a 2 liter round bottomed flask fitted with two double surface Liebigs condensers (20 cm-4 cm). The resultant defatted spores (DFS) were then filtered (porosity grade 3) and dried overnight in air.

To produce the base-hydrolysed (BHS) exines, the defatted spores (DFS) were suspended in 6% w/v aqueous potassium hydroxide and stirred under reflux (conditions as described above) for 6 hours. After filtration (porosity grade 3), this operation was repeated with a fresh sample of the potassium hydroxide solution. Again the suspension was filtered (grade 3) and the resultant solid washed with hot water (three times) and hot ethanol (twice). It was then refluxed in ethanol (conditions as described above) for 2 hours, filtered (grade 3) and dried overnight in air. Subsequently it was thoroughly dried in an oven at 60° C.

To produce the acid-hydrolysed (AHS) exines, the defatted spores were suspended in 85% v/v ortho-phosphoric acid (750 ml), and stirred under reflux (conditions as described above) for 7 days. The solid was then filtered (porosity grade 3), washed with water (5 times, 250 ml), acetone (5 times, 250 ml), ethanol (once, 250 ml), 2M sodium hydroxide (once, 250 ml), water (5 times, 250 ml), acetone (once, 300 ml) and ethanol (once, 300 ml). It was then dried in an oven at 60° C.

Both the BHS and the AHS products contained essentially no nitrogen (assessed by combustion elemental analysis and by IR spectroscopy), indicating removal of proteins and nucleic acids and hence potentially allergenic components of the original spores. They were observed by scanning electron microscope and confocal electron microscopy to be essentially hollow capsules, free of the original inner sporoplasm.

Unless otherwise stated, the exine shells were loaded with oil using the following procedure. The oil was heated to between 40 and 60° C. and mixed with a few drops of ethanol. The relevant exine shells were then added to the resulting emulsion to form a homogeneous mixture. This was subjected to vacuum (30 hPa) for 1 to 2 hours.

Example 1

Stability to UV Light (1)

This example used 25 μm AHS exine shells loaded with either sunflower, rapeseed or soybean oil at an oil:exine weight ratio of 1:1.

The exine shells were loaded with the relevant oil using the procedure outlined above. Each sample was then spread out on a sheet of paper and irradiated with UV light for 2 hours, using a PHILIPS ORIGINAL HOME SOLARIA type HB 171/A, 220-230 volt, 50 Hz, 75 watts, with four PHILIPS CLEO 15 W UV type 30 bulbs. The lamp was held at a distance of 13 cm from the samples.

As controls, unloaded exine samples were subjected to the same treatment.

Following irradiation, the peroxide value (PV) of each sample was determined by titration. For this, the sample was dissolved by stirring in chloroform (10 ml), and acetic acid (15 ml) was added together with a saturated aqueous potassium iodide solution (1 ml). This mixture was shaken in a stoppered flask for 1 minute and set aside, away from the light, for exactly 5 minutes at room temperature. It was then diluted with 75 ml of distilled water and titrated against aqueous sodium thiosulphate (0.01 N), using starch solution as indicator. From this the peroxide value, which is a measure of the amount of active oxygen contained in the sample, could be calculated—degradation of the fat by oxygen generates peroxides, which when treated as described above yield molecular iodine, which is detectable by its reaction with starch to generate colourless sodium iodide. PVs were therefore determined using a standard procedure (IUPAC method 2.500).

The peroxide value of a lipid sample provides an indication of the extent to which the lipid has been degraded to peroxides, and hence of its rancidity. The higher the peroxide value, the more rancid the lipid, and thus the greater the degree of oxidation which it has undergone.

The results are shown in Table 1 below.

TABLE 1

| Oil | Loaded/unloaded exine sample | Exposure to UV (hours) | Peroxide value (PV) (meq/kg) |
|---|---|---|---|
| Sunflower | Unloaded | 0 | 25.3 |
|  | Unloaded | 2 | 31.2 |
|  | Loaded | 2 | 24.9 |
|  | Loaded | 2 | 27.7 |
| Rapeseed | Unloaded | 0 | 5.4 |
|  | Unloaded | 0 | 5.0 |
|  | Unloaded | 2 | 36.4 |
|  | Loaded | 0 | 8.2 |
|  | Loaded | 2 | 5.7 |

TABLE 1-continued

| Oil | Loaded/unloaded exine sample | Exposure to UV (hours) | Peroxide value (PV) (meq/kg) |
|---|---|---|---|
| Soybean | Unloaded | 0 | 10.2 |
| | Unloaded | 2 | 20.6 |
| | Loaded | 2 | 12.2 |

The Table 1 results show that encapsulation of the oils in the exine shells significantly reduces their oxidation rate on exposure to UV light. This makes the exine shells highly suitable for use as vehicles for oxygen- and/or UV-sensitive substances, in particular lipids, which can then be protected against oxidation during their storage prior to use.

Example 2

Stability to UV Light (2)

Duplicate samples were prepared in which echium oil (0.5 g) was added to 25 µm AHS exine shells (0.125 g) to form a homogeneous mixture with an oil:exine weight ratio of 4:1. Unlike in Example 1, the mixture was not subjected to vacuum in order to impregnate the shells with the oil; the oil and exine shells were therefore present as a simply physical mixture, with the majority of the oil outside of the shells.

The samples were irradiated with UV light, and their peroxide values determined both before and after irradiation, as described in Example 1. Again, neat echium oil was used as a control.

The results are shown in Table 2.

TABLE 2

| Oil:exine weight ratio | Exposure to UV (hours) | Peroxide value (meq/kg) |
|---|---|---|
| 1:0 | 0 | 9.0 |
| 1:0 | 0 | 8.5 |
| 1:0 | 2 | 110.1 |
| 1:0 | 2 | 130.3 |
| 4:1 | 2 | 10.1 |
| 4:1 | 2 | 12.5 |

Within experimental error, these data show that the exine shells protect the echium oil to a very significant extent against UV light. This illustrates the natural antioxidant properties of the shells, since in this case most of the oil is likely to be surrounding the exine shells rather than encapsulated within them.

Example 3

Stability Against Aerial Oxidation (1)

This experiment evaluated the protective properties of exine shells against aerial oxidation. Oxidative induction times (OITs), as a measure of the effect of ambient oxygen on oil rancidity, were determined using a METROHM 743 RANCIMAT machine, version 1.0 SRI, with an air flow rate of 20 l/hour and an operating temperature of 50° C. The Rancimat determines the oxidative stability of in particular edible oils and fats, according to the AOCS Air Oxidation Method (AOM-AOCS Cd 12b-92).

All materials—including oils, fats, fatty acid amides and other fatty acid derivatives—have a degree of innate resistance to oxidation. The level of this natural antioxidancy depends on the material itself and any additives it contains, as well as on its prior treatment. Oxidation tends to proceed slowly until the innate resistance is overcome, at which point it accelerates rapidly. The OIT is the length of time before the onset of such acceleration. It is the time limit after which the material under test is generally considered to be rancid.

Using a Rancimat, a stream of filtered and dried air is passed through a sample which is held in a heating block at a predetermined temperature. The effluent air leaving the sample is then bubbled through deionised water, the electrical conductivity of which is constantly measured via a conductivity measuring cell. The sample as it oxidises produces volatile organic compounds including carboxylic acids, predominantly formic acid; the presence of such species in the effluent air produces a corresponding change in conductivity of the initially deionised water. A graph is produced showing the change in conductivity with time, from which the OIT (defined as the point of maximum change in the oxidation rate) can be automatically derived by the Rancimat by reference to the maximum in the second derivative of the conductivity with respect to time.

Three samples were prepared, each in duplicate: fresh echium oil, mixed into glass wool; empty exine shells (obtained as described above) mixed into glass wool; and echium oil loaded into 40 µm AHS exine shells. The oil:exine weight ratio in the latter case was 0.5:1. Confocal electron microscopy showed that in the third sample, the oil was encapsulated by the exine shells.

Air was blown below a loose dispersion of each sample, so as to ensure a large contact surface area. The samples were then assessed using the Rancimat machine, as described above. The results are shown in Table 3.

TABLE 3

| Tube | Glass wool (g) | Product | Oil (g) | Oil:exine weight ratio | Induction time (hours) |
|---|---|---|---|---|---|
| 1 | 1.5 | Empty exines | 0.5 | 0:1 | >190 |
| 2 | 1.5 | | 0.5 | 0:1 | >190 |
| 3 | 1.5 | Oil loaded exines | 1.5 | 0.5:1 | >190 |
| 4 | 1.5 | exines | 1.5 | 0.5:1 | >190 |
| 5 | 1.5 | *Echium* oil | 0.5 | 1:0 | 45 |
| 6 | 1.5 | | 0.5 | 1:0 | 50 |

The Table 3 data show that the exine-encapsulated oil is significantly more resistant to aerial oxidation, and hence significantly more stable. This implies a protective effect due to the exine shell. The protection is likely to be more than simply the shell acting as a physical barrier to the ingress of oxygen, as spore-derived exine shells are known to be at least partially porous.

Example 4

Stability Against Aerial Oxidation (2)

Example 3 was repeated, but using 25 µm AHS exine shells and replacing the encapsulated oil sample with a physical mixture of echium oil and exine shells. The physical mixture contained an oil:exine weight ratio of 5:1 (0.5 g of oil to 0.1 g of the exine shells).

The results are shown in Table 4 below.

TABLE 4

| Tube | Glass wool (g) | Product | Oil (g) | Oil (g) | Oil:exine weight ratio | Induction time (hours) |
|---|---|---|---|---|---|---|
| 1 | 1.033 | Empty exines | 0.350 | 0.000 | 0:1 | >190 |
| 2 | 1.446 |  | 0.408 | 0.000 | 0:1 | >190 |
| 3 | 2.00 | Oil mixed with | 0.600 | 0.500 | 5:1 | >190 |
| 4 | 2.00 | exines | 0.600 | 0.500 | 5:1 | >190 |
| 5 | 0.000 | *Echium* oil | 2.432 | 2.432 | 1:0 | 56 |
| 6 | 0.000 |  | 3.648 | 3.648 | 1:0 | 57 |
| 7 | 1.802 | *Echium* oil | 8.246 | 8.246 | 1:0 | 46 |
| 8 | 2.171 |  | 7.440 | 7.440 | 1:0 | 41 |

Again the echium oil was found to be protected against aerial oxidation by air for at least 190 hours when mixed in excess (5:1) with the exine shells. Since a substantial amount of the oil in this case must be on the outside of the exine shells, this indicates that the shells are themselves acting as antioxidants rather than providing a purely physical barrier to oxygen.

Examples 1 and 3 show that when an oil is encapsulated within an exine shell (ie, housed within the internal cavity of the exine microcapsule with the minimum or no oil on the outside surface—as observed by confocal microscopy), good protection can be observed against UV-induced and aerial oxidation. However when an excess of oil is present, as in this and Example 2, such that there is a significant amount on the outsides of the exine shells and the oil is therefore readily exposed to both air and ambient UV light, we have found that the exine shells themselves act to inhibit oxidation of the oil.

Example 5

Stability to UV Light (3)

Exine shells were loaded with either echium oil or cod liver oil, using the procedure outlined above. The oil:exine weight ratio in each case was 1:1. Both 25 and 40 μm shells were tested, and both AHS (exine alone) and BHS (exine+intine) versions.

Each sample was spread out on a watch glass and irradiated with UV light as described in Example 1. As controls, unencapsulated oil samples were subjected to the same treatment.

The peroxide value (PV) of each sample was determined both before and after irradiation, again as described in Example 1.

The results are shown in Tables 5 to 8 below, for the various types of exine shells tested.

TABLE 5

25 μm AHS

| Oil | Loaded/unloaded exine sample | Exposure to UV (hours) | Peroxide value (PV) (meq/kg) |
|---|---|---|---|
| *Echium* | Unloaded | 0 | 13.5 |
|  | Unloaded | 2 | 67.9 |
|  | Loaded | 0 | 17.1 |
|  | Loaded | 2 | 38.6 |
| Cod liver | Unloaded | 0 | 4.5 |
|  | Unloaded | 2 | 18.3 |
|  | Loaded | 0 | 8.5 |
|  | Loaded | 2 | 9.1 |

TABLE 6

40 μm AHS

| Oil | Loaded/unloaded exine sample | Exposure to UV (hours) | Peroxide value (PV) (meq/kg) |
|---|---|---|---|
| *Echium* | Unloaded | 0 | 13.5 |
|  | Unloaded | 2 | 67.9 |
|  | Loaded | 0 | 20.9 |
|  | Loaded | 2 | 36.7 |
| Cod liver | Unloaded | 0 | 4.5 |
|  | Unloaded | 2 | 18.3 |
|  | Loaded | 0 | 8.5 |
|  | Loaded | 2 | 8.7 |

TABLE 7

25 μm BHS

| Oil | Loaded/unloaded exine sample | Exposure to UV (hours) | Peroxide value (PV) (meq/kg) |
|---|---|---|---|
| *Echium* | Unloaded | 0 | 13.5 |
|  | Unloaded | 2 | 67.9 |
|  | Loaded | 0 | 13.0 |
|  | Loaded | 2 | 17.5 |
| Cod liver | Unloaded | 0 | 4.5 |
|  | Unloaded | 2 | 18.3 |
|  | Loaded | 0 | 4.5 |
|  | Loaded | 2 | 7.3 |

TABLE 8

40 μm BHS

| Oil | Loaded/unloaded exine sample | Exposure to UV (hours) | Peroxide value (PV) (meq/kg) |
|---|---|---|---|
| *Echium* | Unloaded | 0 | 13.5 |
|  | Unloaded | 2 | 67.9 |
|  | Loaded | 0 | 0.0 |
|  | Loaded | 2 | 0.0 |
| Cod liver | Unloaded | 0 | 4.5 |
|  | Unloaded | 2 | 18.3 |
|  | Loaded | 0 | 0.0 |
|  | Loaded | 2 | 0.0 |

These data confirm that encapsulation of the oils into exine shells can significantly reduce their oxidation rate on exposure to UV light.

The results are particularly marked for the 40 μm BHS, which appears to completely protect both oils from oxidation. Moreover, the exine shells in this case appear to "clean up" the oils, reducing their peroxide values even before UV irradiation: this suggests that this BHS is contributing a significant antioxidant effect irrespective of its ability to screen the oil from applied UV light, and that it may even in certain circumstances be capable of removing any previously accrued rancidity.

Example 6

"Clean Up" of Rancid Oils (1)

Example 5 was repeated using cod liver oil, 40 μm exine shells (both AHS and BHS) and an exine:oil weight ratio of 0.5:1, ie, a much higher oil loading. The results are shown in Table 9 below.

TABLE 9

| Sample | PV (meq/kg) before irradiation | PV (meq/kg) after irradiation |
|---|---|---|
| Neat cod liver oil | 4.5 | 18 |
| 40 μm AHS + oil | 10 | 13 |
| 40 μm BHS + oil | 0 | 0 |

Again this demonstrates the ability of the BHS (exine+intine) shells to "clean up" rancidity, the peroxide value for the (exine+oil) sample being lower even than that for the original oil sample.

Example 7

Clean Up of Rancid Oils (2)

Example 6 was repeated, but using an echium oil that already had a peroxide value of 20.5 meq/kg, ie, which was already turning rancid.

The results, prior to irradiation, are shown in Table 10.

TABLE 10

| Sample | Exine:oil weight ratio | PV (meq/kg) before irradiation |
|---|---|---|
| Neat *echium* oil | 0:1 | 20.5 |
| 40 μm AHS + oil | 1:1 | 25.5 |
| 40 μm AHS + oil | 0.5:1 | 26.5 |
| 40 μm BHS + oil | 1:1 | 3 |
| 40 μm BHS + oil | 0.5:1 | 8.5 |

Again these data demonstrate the surprising ability of the 40 μm BHS (ie, exine/intine combination) to "clean up" an already rancid oil. The peroxide value of the original oil sample is significantly reduced after encapsulation in the exine shells. The higher the proportion of exine shells, the greater the effect.

Example 8

Stability Against Aerial Oxidation (3)

Example 3 was repeated but using cod liver oil.

40 μm exine shells (both AHS and BHS) were used for these tests, and were loaded with cod liver oil at oil:exine weight ratios of 1:1, 3:1 and 5:1. Each sample was wedged into the middle of a sample tube between two glass wool wads. A capillary tube was passed through the resulting plug, ensuring that no oil ran down the bottom of the tube. These tubes were then inserted into the heating blocks of the Rancimat machine and air flow commenced.

The results are shown in Table 11 below.

TABLE 11

| Sample | Oil:exine ratio (w/w) | OIT (hours) |
|---|---|---|
| Cod liver oil | 1:0 | 56 |
| Oil:BHS | 5:1 | 59 |
| Oil:BHS | 3:1 | >120 |
| Oil:BHS | 1:1 | >120 |
| Oil:AHS | 5:1 | 73 |
| Oil:AHS | 3:1 | >120 |
| Oil:AHS | 1:1 | >120 |

The Table 11 data again show that the exine-encapsulated oil is significantly more resistant to aerial oxidation, and hence significantly more stable.

The higher the oil loading, the lower the protective effect. This may be because more of the oil is outside of the exine shells and/or only loosely associated with them (encapsulated oil benefits from the natural antioxidancy of the exine shells and may also benefit from some physical protection from the air).

Example 9

Exine Shells as Taste Masking Agents

Exine shells were prepared as described above. They were loaded with cod liver oil (The Boots Company PLC), at an oil:exine weight ratio of 2:1, by subjecting a homogeneous mixture of both components to a vacuum for 1.5 hours.

The resultant material was then tasted by three people. All found it to have a smooth texture and to be free from any oily taste and texture.

This demonstrates the potential for exine shells to be used as taste masking agents in for example pharmaceutical or nutraceutical products, foods and food supplements. Food supplements such as omega-3 oils have for instance what many regard as an unpleasant taste; formulating them with a plant-derived exine shell could therefore serve not only to protect them against oxidation but also to mask their flavour and/or smell, of particular use when they are intended to be added to food or nutraceutical products.

Example 10

Protection of Volatile Actives

This experiment assessed the evaporation rate of a volatile active substance from within spore-derived exine shells.

Exine shells (AHS, 40 μm diameter) were prepared as described above, and loaded with butanol. Alcohols are not only volatile substances, but are also commonly used as diluents in topical formulations such as cosmetics. Impregnation was achieved by "passive contact", ie, by mixing the alcohol with the exine shells at room temperature and pressure and allowing the fluid to permeate into the shells.

Sample A contained 2 ml of neat butanol, as a control; sample B contained 2 ml of butanol encapsulated in 1 g of exine shells.

Each sample was spread on a Petri dish and weighed at 5 minute intervals in order to measure the time taken for all of the encapsulated alcohol to evaporate. All experiments were conducted in triplicate.

The results of these tests are shown in Table 12 below. The half life quoted in each case is a theoretical, calculated indication of the time taken for half the amount of encapsulated alcohol to evaporate.

TABLE 12

| Sample | Evaporation time (min) | Half life (min) |
|---|---|---|
| A | 200 | 61 |
| B | 300 | 115 |

Table 12 shows that encapsulation of a volatile alcohol within an exine shell can considerably inhibit its release by evaporation. A protective coating, for example a lipid coating layer, could be applied to the shells in order to slow evaporative loss yet further and thus to protect volatile active substances in formulations prepared according to the invention.

Example 11

High Active Substance Loadings

Oil was stirred with 25 µm AHS exine shells to form a homogeneous mixture which was then subjected to vacuum (30 kPa) for 2 hours in order to impregnate the shells with the oil. The oils used were soybean oil, sunflower oil, echium oil and rapeseed oil, each up to 3 g per gram of exine shells and in the case of the cod liver oil up to 3.5 g per gram of exine shells.

It was found that even at these relatively high loadings, the oil-loaded exine shells behaved as powders, confirming effective encapsulation of the oils. This was further confirmed by confocal microscopy. It demonstrates one of the advantages of using spore-derived exine shells as delivery vehicles for active substances. It also shows the suitability of the shells as vehicles in powder formulations, for instance for topical delivery of cosmetic substances, cleaning products or laundry products, or for delivery of pharmaceutically or nutraceutically active substances, food supplements and the like.

At loading levels at and above 5 g of oil per gram of exine shells, the samples behaved more as pastes, indicating that a significant proportion of the oil was then outside of the exine shells. Such formulations might be suitable for application as a cream or ointment, for example, or might have application in certain types of food product. At loading levels at and below 2 g of oil per gram of exine shells, the powders were fine, free flowing powders and reasonably dry to the touch.

Example 12

Cod liver oil was added to exine shells of various types and in various oil:exine weight ratios, and the rate of change in peroxide value for each sample was measured over a period of eleven weeks following the mixing. All mixtures were prepared in transparent bottles at room temperature, using 50 ml of the oil, and samples were removed for analysis as necessary. The exine shells sedimented at the bottom of the bottles; no agitation was effected and the only movement of the oil in the bottles was thus due to convection currents. The bottles were closed during storage, but each contained about 3 ml of air which was free to circulate above the surface of the oil. They were exposed during storage to ambient light conditions.

The bottles contained the following samples (except where otherwise indicated, the exine shells were derived from *Lycopodium clavatum*, as per Examples 1 to 11 above):

Bottle A cod liver oil (control)
Bottle B 25 µm AHS exine shells at an exine:oil ratio of 1.0 g:50 ml (2% w/w exine)
Bottle C 25 µm AHS exine shells at an exine:oil ratio of 0.5 g:50 ml (1% w/w exine)
Bottle D 25 µm AHS exine shells at an exine:oil ratio of 0.1 g:50 ml (0.2% w/w exine)
Bottle E 25 µm BHS exine shells at an exine:oil ratio of 1.0 g:50 ml (2% w/w exine)
Bottle F 25 µm BHS exine shells at an exine:oil ratio of 0.5 g:50 ml (1% w/w exine)
Bottle G 25 µm BHS exine shells at an exine:oil ratio of 0.1 g:50 ml (0.2% w/w exine)
Bottle H acetolysed* ryegrass exine shells at an exine:oil ratio of 0.5 g:50 ml (1% w/w exine)
Bottle I acetolysed* ryegrass exine shells (subjected to 6% (w/v) aqueous NaOH for 2 hours at 60° C. following the acetolysis), at an exine:oil ratio of 0.5 g:50 ml (1% w/w exine).

*(The acetolysed ryegrass exines were prepared by adding 20 ml of a 19:1 mixture of acetic anhydride and concentrated sulphuric acid to 1.0 g of ryegrass pollen and stirring the resultant mixture for 15 minutes at 100° C.)

A further sample was prepared and tested, containing 25 µm AHS exine shells which had been subjected to an additional bleaching step as described by G. Erdtman in *Svensk Botanisk Tidskrift*, 1960, 54(4): 561-564. These were included in the oil at an exine:oil ratio of 0.5 g:50 ml (1% w/w exine).

The results are shown in the tables in Appendix I. In these tables, the "Date" column refers to the number of weeks following mixing (at Date=0) of the oil and exine shells. The "Initial Vol" and "Final Vol" columns refer to the initial and final titration volumes recorded during the peroxide value titrations. The peroxide values (PV) are expressed in meq/kg. Those quoted at Date=0 are averages of six titrations.

It can be seen from these data that even at very low concentrations (0.2% w/w exine), all of the mixtures according to the invention reduced the rate of increase in PV compared to the untreated oil control. At such concentrations, very little oil is encapsulated within the exine shells; thus the chemical antioxidant effect of the shells is readily apparent. They may therefore be used to improve the stability of oxygen-sensitive active substances, in particular oils, and thereby to improve the shelf life of formulations containing such active substances.

It is also of note that in these samples, only a small proportion of the oil is in contact with the sedimented exine shells at any one time. The movement of oil molecules through the bulk liquid, for example due to convection currents, is believed to allow sufficient contact between the oil and the exine shells to provide a protective antioxidant effect throughout the liquid.

These data also show that the bleached exine shells appear able to "clean up" existing oxidative degradation. Addition of the shells to the oil resulted in a reduction in its initial peroxide value, an effect which resulted in the peroxide value remaining lower than its initial value throughout the first few weeks of storage.

Example 13

Exine shells from *Lycopodium clavatum* were loaded with cod liver oil as in the previous examples, and the peroxide values of the resultant samples measured over after a period of two hours, both with and without UV irradiation. The results are shown in Tables 13 to 18 below. As in Appendix I, the "Initial" and "Final" columns refer to the initial and final titration volumes recorded during the peroxide value titrations. The peroxide values (PV) are expressed in meq/kg.

The Table 13 and 14 data are for 25 µm AHS exines, at an exine:oil weight ratio of 1:5 (i.e. 16.67% w/w exine), with and without UV respectively.

The Table 15 and 16 data are for 25 µm AHS exines, at an exine:oil weight ratio of 1:6 (i.e. 14.29% w/w exine), with and without UV respectively.

The Table 17 and 18 are for cod liver oil alone (control), with and without UV respectively.

TABLE 13

| Expt. No. | Exine weight (g) | Cod liver oil weight (g) | Initial | Final | Difference | PV |
|---|---|---|---|---|---|---|
| A | 0.21 | 1.01 | 23.5 | 24.3 | 0.8 | 7.9 |
| B | 0.21 | 1.00 | 24.3 | 25.5 | 1.2 | 12.0 |

TABLE 14

| Expt. No. | Exine weight (g) | Cod liver oil weight (g) | Initial | Final | Difference | PV |
|---|---|---|---|---|---|---|
| A | 0.21 | 1.01 | 22.4 | 23.0 | 0.6 | 5.9 |
| B | 0.20 | 1.01 | 23.0 | 23.5 | 0.5 | 4.9 |

TABLE 15

| Expt. No. | Exine weight (g) | Cod liver oil weight (g) | Initial | Final | Difference | PV |
|---|---|---|---|---|---|---|
| A | 0.16 | 1.02 | 26.0 | 26.8 | 0.8 | 7.8 |
| B | 0.16 | 1.01 | 26.8 | 28.1 | 1.3 | 12.9 |

TABLE 16

| Expt. No. | Exine weight (g) | Cod liver oil weight (g) | Initial | Final | Difference | PV |
|---|---|---|---|---|---|---|
| A | 0.16 | 1.00 | 6.6 | 7.0 | 0.4 | 4.0 |
| B | 0.16 | 1.00 | 7.0 | 7.3 | 0.3 | 3.0 |

TABLE 17

| Expt. No | Oil weight (g) | Initial | Final | Difference | PV |
|---|---|---|---|---|---|
| A | 1.00 | 5.5 | 9.4 | 3.9 | 39.0 |
| B | 1.00 | 9.4 | 13.6 | 4.2 | 42.0 |
| C | 1.00 | 13.6 | 17.0 | 3.4 | 34.0 |

TABLE 18

| Expt. No | Oil mass (g) | Initial | Final | Difference | PV |
|---|---|---|---|---|---|
| A | 1.01 | 19.7 | 20.3 | 0.6 | 5.9 |
| B | 1.00 | 20.7 | 21.6 | 0.9 | 9.0 |
| C | 0.99 | 21.6 | 22.5 | 0.9 | 9.1 |

These data show that even (indeed, especially) on exposure to UV radiation, oxidation of the two oil/exine mixtures according to the invention is significantly inhibited compared to that of the oil alone, at both the exine concentrations tested.

From all the above examples, it is clear that exine shells of naturally occurring spores can be used as antioxidants, across a range of active substance:exine concentration ratios. Indeed, antioxidant activity is shown at exine concentrations as low as 0.2% w/w, as well as at higher exine concentrations up to about 67% w/w. Antioxidant activity at exine concentrations between these upper and lower values is of course also expected; indeed, in other experiments an antioxidant effect has also been observed in lipid formulations containing 5% w/w of exine shells.

APPENDIX I

| Date | Oil Mass (g) | Initial Vol (ml) | Final Vol (ml) | Difference (ml) | PV |
|---|---|---|---|---|---|
| Bottle A | | | | | |
| 0 | | | | | 7.3 |
| 1 | 1.00 | 10.1 | 11.2 | 1.1 | 11.0 |
| 2 | 1.01 | 28.2 | 29.9 | 1.7 | 16.8 |
| 3 | 1.00 | 0.0 | 1.9 | 1.9 | 19.0 |
| 4 | 1.00 | 6.4 | 8.4 | 2.0 | 20.0 |
| 5 | 1.00 | 0.0 | 2.4 | 2.4 | 24.0 |
| 6 | 1.01 | 0.0 | 2.4 | 2.4 | 23.8 |
| 7 | 1.00 | 20.8 | 23.2 | 2.4 | 24.0 |
| 8 | 1.03 | 2.8 | 5.8 | 3.0 | 29.2 |
| 9 | 1.00 | 0.1 | 3.2 | 3.1 | 31.0 |
| 10 | 1.01 | 0.1 | 3.3 | 3.2 | 31.7 |
| 11 | 0.99 | 0.0 | 3.4 | 3.4 | 34.3 |
| Bottle B | | | | | |
| 0 | | | | | 7.3 |
| 1 | 1.00 | 11.2 | 12.2 | 1.0 | 10.0 |
| 2 | 1.00 | 29.9 | 30.9 | 1.0 | 10.0 |
| 3 | 1.02 | 1.9 | 2.9 | 1.0 | 9.8 |
| 4 | 1.00 | 8.4 | 9.8 | 1.4 | 14.0 |
| 5 | 1.03 | 2.4 | 4.0 | 1.6 | 15.5 |
| 6 | 1.00 | 2.4 | 4.0 | 1.6 | 16.0 |
| 7 | 1.00 | 23.2 | 24.9 | 1.7 | 17.0 |
| 8 | 1.02 | 5.8 | 7.6 | 1.8 | 17.7 |
| 9 | 1.01 | 3.2 | 5.6 | 2.4 | 23.8 |
| 10 | 1.01 | 3.3 | 5.3 | 2.0 | 19.8 |
| 11 | 1.00 | 3.4 | 5.6 | 2.2 | 22.0 |
| Bottle C | | | | | |
| 0 | | | | | 7.3 |
| 1 | 1.01 | 12.2 | 13.0 | 0.8 | 7.9 |
| 2 | 1.00 | 30.9 | 32.0 | 1.1 | 11.0 |
| 3 | 1.00 | 2.9 | 4.2 | 1.3 | 13.0 |
| 4 | 1.04 | 9.8 | 11.5 | 1.7 | 16.4 |
| 5 | 1.00 | 4.0 | 5.5 | 1.5 | 15.0 |
| 6 | 1.03 | 4.0 | 5.5 | 1.5 | 14.6 |
| 7 | 1.02 | 24.9 | 26.7 | 1.8 | 17.7 |
| 8 | 1.00 | 7.6 | 9.4 | 1.8 | 18.0 |
| 9 | 1.01 | 5.6 | 7.6 | 2.0 | 19.8 |
| 10 | 1.01 | 5.3 | 7.4 | 2.1 | 20.8 |
| 11 | 1.00 | 5.6 | 7.4 | 1.8 | 18.0 |
| Bottle D | | | | | |
| 0 | | | | | 7.3 |
| 1 | 1.00 | 13.0 | 14.3 | 1.3 | 13.0 |
| 2 | 1.00 | 32.0 | 33.5 | 1.5 | 15.0 |
| 3 | 1.02 | 4.2 | 5.7 | 1.5 | 14.7 |
| 4 | 1.00 | 11.5 | 13.2 | 1.7 | 17.0 |
| 5 | 1.01 | 5.5 | 7.5 | 2.0 | 19.8 |
| 6 | 1.00 | 5.5 | 7.4 | 1.9 | 19.0 |
| 7 | 1.00 | 26.7 | 28.9 | 2.2 | 22.0 |
| 8 | 1.01 | 9.4 | 11.8 | 2.4 | 23.8 |
| 9 | 0.99 | 7.6 | 9.9 | 2.3 | 23.2 |
| 10 | 1.00 | 7.4 | 10.1 | 2.7 | 27.0 |
| 11 | 1.00 | 7.4 | 10.1 | 2.7 | 27.0 |
| Bottle E | | | | | |
| 0 | | | | | 7.3 |
| 1 | 1.01 | 14.3 | 15.3 | 1.0 | 9.9 |
| 2 | 1.02 | 33.5 | 34.7 | 1.2 | 11.8 |
| 3 | 1.00 | 5.7 | 6.9 | 1.2 | 12.0 |
| 4 | 1.03 | 13.2 | 14.9 | 1.7 | 16.5 |
| 5 | 1.01 | 7.5 | 9.3 | 1.8 | 17.8 |
| 6 | 0.99 | 7.4 | 8.8 | 1.4 | 14.1 |
| 7 | 1.01 | 28.9 | 30.7 | 1.8 | 17.8 |
| 8 | 1.00 | 11.8 | 13.9 | 2.1 | 21.0 |
| 9 | 0.99 | 9.9 | 11.9 | 2.0 | 20.2 |

APPENDIX I-continued

| Date | Oil Mass (g) | Initial Vol (ml) | Final Vol (ml) | Difference (ml) | PV |
|---|---|---|---|---|---|
| 10 | 0.99 | 10.1 | 12.5 | 2.4 | 24.2 |
| 11 | 1.00 | 10.1 | 12.2 | 2.1 | 21.0 |
| Bottle F | | | | | |
| 0 | | | | | 7.3 |
| 1 | 1.01 | 15.3 | 16.4 | 1.1 | 10.9 |
| 2 | 1.01 | 34.7 | 36.0 | 1.3 | 12.9 |
| 3 | 1.01 | 6.9 | 8.2 | 1.3 | 12.9 |
| 4 | 1.00 | 14.9 | 16.3 | 1.4 | 14.0 |
| 5 | 1.01 | 9.3 | 11.0 | 1.7 | 16.8 |
| 6 | 1.00 | 8.8 | 10.4 | 1.6 | 16.0 |
| 7 | 1.00 | 30.7 | 32.5 | 1.8 | 18.0 |
| 8 | 1.03 | 13.9 | 16.2 | 2.3 | 22.3 |
| 9 | 1.00 | 11.9 | 14.3 | 2.4 | 24.0 |
| 10 | 0.99 | 12.5 | 15.3 | 2.8 | 28.3 |
| 11 | 1.00 | 12.2 | 14.8 | 2.6 | 26.0 |
| Bottle G | | | | | |
| 0 | | | | | 7.3 |
| 1 | 1.01 | 16.4 | 17.3 | 0.9 | 8.9 |
| 2 | 1.01 | 2.0 | 3.0 | 1.0 | 9.9 |
| 3 | 1.00 | 8.2 | 9.4 | 1.3 | 13.0 |
| 4 | 1.00 | 16.3 | 18.0 | 1.7 | 17.0 |
| 5 | 1.01 | 11.0 | 12.8 | 1.8 | 17.8 |
| 6 | 1.02 | 10.4 | 12.2 | 1.8 | 17.7 |
| 7 | 1.01 | 32.6 | 34.8 | 2.2 | 21.8 |
| 8 | 1.02 | 16.2 | 18.8 | 2.4 | 23.5 |
| 9 | 1.00 | 14.3 | 17.0 | 2.7 | 27.0 |
| 10 | 1.00 | 16.3 | 18.0 | 2.7 | 27.0 |
| 11 | 1.02 | 14.8 | 17.7 | 2.9 | 28.4 |
| 0.5 g Bleached 25 μm AHS | | | | | |
| 0 | | | | | 7.3 |
| 1 | 1.01 | 17.3 | 17.7 | 0.4 | 4 |
| 2 | 1.01 | 3 | 3.4 | 0.4 | 4 |
| 3 | 1 | 9.5 | 10.1 | 0.6 | 6 |
| 4 | 1.01 | 18 | 18.6 | 0.6 | 5.9 |
| 5 | 1.03 | 12.8 | 13.7 | 0.9 | 8.7 |
| 6 | 1.03 | 12.2 | 13 | 0.8 | 7.8 |
| 7 | 1.01 | 34.8 | 35.9 | 1.1 | 10.9 |
| 8 | 1.01 | 18.8 | 20.2 | 1.4 | 13.9 |
| 9 | 1.01 | 17 | 18.6 | 1.6 | 15.8 |
| 10 | 1 | 18 | 19.5 | 1.5 | 15 |
| 11 | 1 | 17.7 | 19.7 | 2 | 20 |
| Bottle H | | | | | |
| 0 | | | | | 7.3 |
| 1 | 1.01 | 17.7 | 18.7 | 1.0 | 9.9 |
| 2 | 1.01 | 3.4 | 4.5 | 1.1 | 10.9 |
| 3 | 1.00 | 10.1 | 11.3 | 1.2 | 12.0 |
| 4 | 1.01 | 18.6 | 20.3 | 1.7 | 16.8 |
| 5 | 1.01 | 13.7 | 15.3 | 1.6 | 15.8 |
| 6 | 1.01 | 13.0 | 14.6 | 1.6 | 15.8 |
| 7 | 1.01 | 35.9 | 37.8 | 1.9 | 18.8 |
| 8 | 0.99 | 20.2 | 22.5 | 2.3 | 23.2 |
| 9 | 1.00 | 18.6 | 20.9 | 2.3 | 23.0 |
| 10 | 0.98 | 19.5 | 22.3 | 2.8 | 28.6 |
| 11 | 1.04 | 19.7 | 22.8 | 3.1 | 29.8 |
| Bottle I | | | | | |
| 0 | | | | | 7.3 |
| 1 | 1.00 | 18.7 | 19.7 | 1.0 | 10.0 |
| 2 | 1.03 | 4.5 | 5.5 | 1.0 | 9.7 |
| 3 | 1.01 | 11.3 | 12.5 | 1.2 | 11.9 |
| 4 | 1.00 | 20.3 | 21.8 | 1.5 | 15.0 |
| 5 | 1.03 | 15.3 | 16.9 | 1.6 | 15.5 |
| 6 | 1.00 | 14.6 | 16.3 | 1.7 | 17.0 |
| 7 | 1.03 | 37.8 | 39.9 | 2.1 | 20.4 |
| 8 | 1.01 | 22.5 | 25.0 | 2.5 | 24.8 |
| 9 | 0.99 | 20.9 | 23.7 | 2.8 | 28.3 |
| 10 | 1.00 | 22.3 | 25.2 | 2.9 | 29.0 |
| 11 | 1.00 | 22.8 | 26.1 | 3.3 | 33.0 |

N.B. Peroxide Value for data "0" is a average of 6 titrations
Standard Deviation = 1.64

What is claimed is:

1. A method of screening for a composition comprising an active substance for use as, or inclusion in, a formulation, the method comprising:
   a) measuring an initial oxidative stability value of the active substance;
   b) mixing an active substance with an exine shell of a naturally occurring spore, or a fragment thereof, to produce a composition;
   c) measuring a post-mixing oxidative stability value for the active substance in the composition or for the composition; and
   d) if the post-mixing oxidative stability value of the active substance or composition is equal to, or greater than, the initial value, selecting the composition for use as, or inclusion in, a formulation.

2. The method of claim 1, additionally comprising enclosing the formulation in a container or package.

3. The method of claim 1, wherein the formulation is marketed with an indication that the active substance or composition has been tested to assure oxidative stability and/or any property affected by oxidative stability.

4. The method of claim 3, wherein said marketing is selected from the group consisting of:

a) enclosing the formulation in a container or package that comprises said indication;

b) packaging the formulation with a package insert that comprises said indication;

c) providing said indication in a publication that describes the formulation; and d) providing said indication in a commercial aired on the radio, television, or the internet.

5. The method of claim 3, wherein said property affected by oxidative stability is selected from the group consisting of:

a) the chemical structure of the active substance;

b) the purity of the active substance in the formulation;

c) a physical property of the active substance or formulation;

d) the activity of the active substance;

e) bioavailability of the active substance;

f) the taste of the active substance or formulation;

g) the smell of the active substance or formulation;

h) the appearance of the active substance or formulation;

i) the concentration of an oxidation product of the active substance in the formulation; and/or j) shelf-life of the formulation.

6. The method of claim 5, wherein the active substance comprises a lipid.

7. The method of claim 6, wherein the property affected by oxidative stability comprises the concentration of an oxidation product of said lipid.

8. The method of claim 7, wherein the property is selected from the group consisting of peroxide value and free fatty acid content.

9. A method for reducing the amount of a previously formed oxidation product from an active substance or formulation, the method comprising:

a) determining that the active substance or formulation has already undergone at least some oxidative degradation by measuring a property affected by oxidation;

b) selecting an exine shell of a naturally occurring spore, or a fragment thereof, said exine shell being capable of reducing the amount of a previously formed oxidation product from an active substance or formulation; and c) mixing the exine shell or fragment with the active substance or adding the exine shell or fragment to the formulation to reduce the amount of a previously formed oxidation product from the active substance or formulation.

10. The method of claim 1 or 9, wherein the active substance is mixed with the exine shell or fragment to produce a composition that comprises between 0.1 and 16 percent by weight exine shell and/or fragment thereof.

11. The method of claim 10, wherein the composition comprises between 3 and 16 percent by weight exine shell and/or fragment thereof.

12. The method of claim 1 or 9, wherein the exine shell or fragment comprises no more than 5 percent nitrogen by weight, and the method does not comprise adding any spore protein to the active substance and/or formulation.

13. The method of claim 1 or 9, wherein the exine shell or fragment is derived from *Lycopodium clavatum*.

14. The method of claim 1 or 9, wherein the method additionally comprises adding the active substance and/or the formulation to a food or beverage or to an ingredient for a food or beverage.

15. The method of claim 1 or 9, wherein the method additionally comprises adding the active substance and/or the formulation to a pharmaceutical, dietetic, or cosmetic formulation.

16. The method of claim 9, wherein the property affected by oxidation is selected from the group consisting of:
    a) the chemical structure of the active substance;
    b) the purity of the active substance in the formulation;
    c) a physical property of the active substance or formulation;
    d) the activity of the active substance;
    e) bioavailability of the active substance;
    f) the taste of the active substance or formulation;
    g) the smell of the active substance or formulation;
    h) the appearance of the active substance or formulation;
    i) the concentration of an oxidation product of the active substance in the formulation; and/or
    j) shelf-life of the formulation.

17. The method of claim 16, wherein the active substance comprises a lipid.

18. The method of claim 17, wherein the property affected by oxidation comprises the concentration of an oxidation product of said lipid.

19. The method of claim 18, wherein the property is selected from the group consisting of peroxide value and free fatty acid content.

20. The method of claim 9, wherein the method additionally comprises, after said mixing of (c), measuring a property affected by oxidation.

21. The method of claim 20, wherein the property affected by oxidation that is measured prior to said selecting of (a) provides an initial oxidative degradation value and the same property is measured after said mixing of (c) to provide a final oxidative degradation value, and the final oxidative degradation value is lower than the initial oxidative degradation value.

22. The method of claim 9, wherein the exine shell or fragment thereof is separated from the active substance or formulation a period of time after said mixing of (c).

23. The method of claim 22, wherein the method additionally comprises:
    after said mixing of (c), measuring the same property affected by oxidation to provide a final oxidative degradation value;
    wherein the exine shell or fragment thereof is separated from the active substance or formulation after determining that the final oxidative degradation value is lower than the initial oxidative degradation value.

24. The method of claim 1 or 9, wherein the active substance is mixed with the exine shell or fragment to produce a composition that contains the active substance and exine shells at an active substance:exine shell weight ratio of from 0.01:1 to 35:1.

25. The method of claim 1 or 9, wherein the active substance is mixed with the exine shell or fragment to produce a composition that contains the active substance and exine shells at an active substance:exine shell weight ratio of from 0.1:1 to 5:1.

* * * * *